United States Patent
Grotjahn

(10) Patent No.: US 8,501,032 B2
(45) Date of Patent: Aug. 6, 2013

(54) CATALYSTS FOR ALKENE ISOMERIZATION AND CONJUGATING DOUBLE BONDS IN POLYUNSATURATED FATS AND OILS

(75) Inventor: Douglas Grotjahn, San Diego, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 360 days.

(21) Appl. No.: 12/669,959

(22) PCT Filed: Jul. 25, 2008

(86) PCT No.: PCT/US2008/071241
§ 371 (c)(1),
(2), (4) Date: May 26, 2010

(87) PCT Pub. No.: WO2009/015360
PCT Pub. Date: Jan. 29, 2009

(65) Prior Publication Data
US 2010/0228031 A1    Sep. 9, 2010

Related U.S. Application Data

(60) Provisional application No. 60/952,218, filed on Jul. 26, 2007, provisional application No. 61/039,703, filed on Mar. 26, 2008.

(51) Int. Cl.
*C09K 3/32*    (2006.01)
*C07F 15/00*    (2006.01)

(52) U.S. Cl.
USPC .................. 252/182.11; 548/101; 502/162

(58) Field of Classification Search
USPC .................. 548/101; 252/182.11; 502/162
See application file for complete search history.

(56) References Cited

FOREIGN PATENT DOCUMENTS
WO    WO 2007/035901 A2  *  3/2007

OTHER PUBLICATIONS

Grotjahn, D. et al.: Extensive Isomerization of alkenes using a bifunctional catalyst: An alkene Zipper. J. Am. Chem. Soc., vol. 129, pp. 9592-9593, 2007.*
Grotjahn, D. et al.: Changes in coordination of sterically demanding hybrid imidazolylphosphine ligands on Pd(0) and Pd(II). J. Am. Chem. Soc., vol. 128, pp. 438-453, 2006.*

* cited by examiner

*Primary Examiner* — Charanjit Aulakh
(74) *Attorney, Agent, or Firm* — Gregory P. Einhorn; Gavrilovich, Dodd & Lindsey LLP

(57) ABSTRACT

The invention provides ruthenium-comprising catalysts, and methods of making and using them, for conjugating double bonds in polyunsaturated hydrocarbons, including polyunsaturated fatty acid derivatives, such as natural fats and oils which comprise (contain) more than one carbon to carbon double bond—where the double bonds are separated by, e.g., a methylene, ethylene or propylene or longer group. The invention provides compositions and methods for treating fats and oils comprising "interrupted" (e.g., "methylene-, ethylene- or propylene-interrupted") double bonds to generate isomers with "conjugated" double bonds. The invention also provides compositions, and methods of making and using them, for making catalysts on a solid support. In one aspect, these catalysts are for alkene isomerization or exchange of alkene hydrogens for other isotopes. The invention provides heterocyclic resin-based compositions, and methods of using them, for making catalysts for alkene isomerization and exchange of hydrogens for deuterium or tritium isotopes.

20 Claims, No Drawings

CATALYSTS FOR ALKENE ISOMERIZATION AND CONJUGATING DOUBLE BONDS IN POLYUNSATURATED FATS AND OILS

RELATED APPLICATIONS

This application is a national phase application claiming benefit of priority under 35 U.S.C. §371 to Patent Convention Treaty (PCT) International Application Serial No: PCT/US2008/071241, filed Jul. 25, 2008, which claims benefit of priority to U.S. Provisional Patent Application Ser. No. 60/952,218, filed Jul. 26, 2007, and U.S. Ser. No. 61/039,703, filed Mar. 26, 2008. The aforementioned applications are expressly incorporated herein by reference in their entirety and for all purposes.

FIELD OF THE INVENTION

This invention relates generally to the fields of transition metal catalysts and, food preparation, and to uses of fats and oils in industrial processes. In particular, the invention provides catalysts for conjugating double bonds in polyunsaturated organic molecules, e.g., fatty acid derivatives, and in any organic molecule containing more than one double bond. The invention also provides compositions, and methods of making and using them, for making catalysts on a solid support. In one aspect, these catalysts are for alkene isomerization or exchange of alkene hydrogens for other isotopes. The invention provides heterocyclic immobilized compositions (e.g., immobilized on resins), and methods of using them, for making catalysts for alkene isomerization and exchange of hydrogens for deuterium or tritium isotopes.

BACKGROUND

In the prior art there are a number of compositions and methods for harnessing the ability of a transition metal to migrate a double bond along a hydrocarbon chain. It is typically the group 8, 9 and 10 transition metals that are employed for this transformation. A variety of ruthenium derivatives have been used for isomerization reactions.

For natural oils containing more than one carbon to carbon double bond, the double bonds are generally separated by a methylene group, commonly referred to as being "methylene interrupted." These fats and oils have nutritional benefits; however, the methylene interruption limits their use in industrial applications, including polymerization where they could find use as coatings, adhesives and the like. For these fats and oils to be so used industrially, they need to polymerize rapidly. For this to occur, it is advantageous to have the double bonds adjacent to one another or "conjugated", i.e., the methylene interrupt is shifted or relocated. In addition, research has shown that conjugated isomers of certain compounds (such as linoleic acid, which has two methylene interrupted double bonds) may have beneficial effects on health.

There are a number of compositions and methods known for harnessing the ability of a transition metal to migrate a double bond across a hydrocarbon chain. It is typically the group 8, 9 and 10 transition metals that are employed for this transformation. A variety of ruthenium derivatives have been used for isomerization reactions. Most of these derivatives are soluble in solvents.

SUMMARY OF THE INVENTION

The invention provides ruthenium-comprising catalysts, and methods of making and using them, for conjugating double bonds (e.g., moving methylene interrupted double bonds such that they become located adjacent to one another) in polyunsaturated hydrocarbons, including polyunsaturated fatty acid derivatives, such as natural fats and oils which comprise (contain) more than one carbon to carbon double bond—where in one aspect the double bonds are separated by a methylene group. The invention provides compositions (e.g., catalysts) and methods for treating fats and oils comprising "methylene interrupted" double bonds to generate isomers with "conjugated" double bonds. However, the invention also provides compositions (e.g., catalysts) and methods for treating fats and oils comprising double bonds "interrupted" by longer than methylene groups to generate isomers with "conjugated" (adjacent) double bonds.

The invention provides ruthenium derivatives for use (e.g., as catalysts) in isomerization reactions, e.g., for conjugating double bonds in hydrocarbons, such as for treating fats and oils comprising "interrupted" (e.g., "methylene interrupted") double bonds to generate isomers with "conjugated" double bonds; and in one aspect these ruthenium derivatives are insoluble in one or more solvents.

The invention provides bifunctional alkene isomerization catalysts, such as those of formula 1, and its derivatives, for conjugating or isomerizing fatty acid derivatives, including natural oils and fats, such as those of linoleic and linolenic acid. The catalysts of this invention can isomerize or conjugate these compounds (e.g., natural oils and fats) either in acid or in ester form (e.g. as methyl esters), either exclusively or primarily to mixtures of the conjugated isomers. One key feature of the catalyst of the invention Formula 1 is that under the same conditions it leaves oleic acid derivatives unchanged or nearly so. Thus, catalyst 1 can convert polyunsaturated derivatives containing skipped double bonds to their conjugated isomers without affecting monounsaturated derivatives.

Formula 1 (including the several genuses of structures 1, 2, 3, 4, 2a, 2b and 2c)

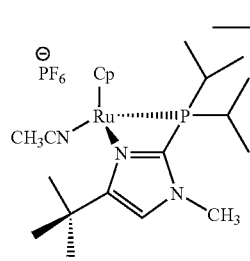

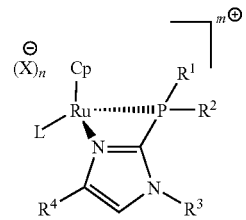

-continued

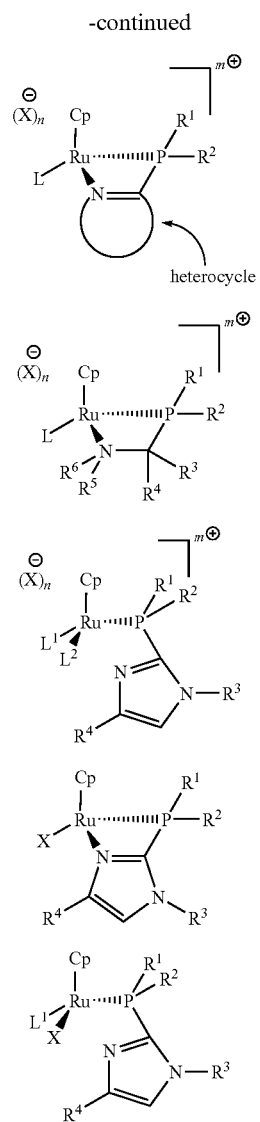

In alternative aspects, the invention provides compounds having formula 2, 2a, 2b, 2c, 3 and 4 structures, where formula 2, 2a, 2b, 2c, 3 and 4 structures illustrate independent exemplary genuses of structures of this invention wherein: ligand L also can be $CH_3CN$ or derivatives thereof, halide, hydride, carboxylate, sulfonate, or any substituted derivatives thereof, or any neutral or anionic ligand, for example alkene, with appropriate balance of charge m on the cation by n anion(s); $R^1$, $R^2$, $R^3$, and $R^4$ can each separately and independently be hydrogen, $CH(CH_3)_2$, $C(CH_3)_2$, or any alkyl or aryl group, including heteroaryl, or any other substituent.

In alternative aspects, the invention provides compounds having Formula 2a, which is a variant of 2 in which two ligands $L^1$ and $L^2$ which may be the same or different are present, which can each separately and independently be $CH_3CN$ or derivatives thereof, halide, hydride, carboxylate, sulfonate, or any substituted derivatives thereof, or any neutral or anionic ligand, for example alkene, with appropriate balance of charge m on the cation by n anion(s). Formula 2b and formula 2c are more specific variants of 2 and 2a, respectively, wherein X is an anionic ligand (e.g. halide, hydride, carboxylate, sulfonate, or any substituted derivatives thereof) and the overall charge of the complex is zero.

In alternative aspects, the invention provides compounds having Formula 3, which is more general version of 2 in which the imidazole has been replaced by that of another heterocycle, and formula 4 is a more general version in which the carbon between P and N bears two R groups, $R^3$ and $R^4$. In addition, the Cp ligand ($C_5H_5$) in Formulas 1, 2, 2a, 2b, 2c, 3, and 4 could be substituted with any alkyl or aryl group or groups, including heteroaryl, or any other substituents. Moreover, the Cp ligand could be replaced with ligands such as indenyl or benzene or any of its derivatives (substituted with any alkyl or aryl group or groups, including heteroaryl, or any other substituents), Tp (tris-pyrazolylborate) or any of its derivatives (substituted with any alkyl or aryl group or groups, including heteroaryl, or any other substituents), or any ligand of similar structure capable of providing an active catalyst.

The compounds of this invention can be made using any one of Schemes Ito XI, as described below.

The invention also provides imidazolyl resin-, solid-support-, or nanoparticle-based (e.g., resin-, solid-support-, or microsphere- or nanoparticle-immobilized) compositions, and methods of making and using them, for making catalysts for alkene isomerization.

The invention provides methods for converting an imidazole with one nitrogen unsubstituted to a salt, and for isomerizing alkenes comprising the protocol of "Scheme 1", below. For example, in one aspect, the invention provides methods for converting 4(5)-tert-butylimidazole (compound 9) to its sodium salt (compound 10), and displacing a benzylic chloride on Merrifield resin (8) to produce an imidazolyl resin (compound II), using a protocol, and equivalents thereof, as set forth in Scheme 1, below.

The invention also provides an immobilized catalyst (e.g., a resin-based catalyst) for alkene isomerization, wherein the catalyst has a formula as set forth in compound 13a or compound 13b of Scheme 1, or equivalents.

The invention provides products of manufacture, kits and formulations, including liquid formulations, comprising: a composition of the invention, an alkene isomerization catalyst of the invention, or an immobilized catalyst of the invention (e.g., a resin-based catalyst) for alkene isomerization of the invention, or a combination thereof.

The invention provides solid or semisolid supports and resins, e.g., ion exchange or any chromatography resin(s), comprising a composition of the invention, an alkene isomerization catalyst of the invention, or an immobilized catalyst of the invention (e.g., as a resin-based catalyst) for alkene isomerization, or a combination thereof; and in alternative embodiments the composition or catalyst of the invention is ionically or covalently attached to the resin or solid or semisolid support. The invention provides products of manufacture, including any solid or semisolid (e.g., gel) composition, wherein a composition or catalyst of the invention is ionically or covalently attached. In alternative embodiments, the resin is a cellulose resin (e.g., a ethylsulfoxycellulose, a carboxymethyl cellulose or a hydroxyethyl cellulose resin), a fluorine-containing resin, a polymeric resin, urethane resin, an epoxy resin, a polyester resin, a phenol resin, a melamine resin, and/or a silicone resin. In alternative aspects, the solid support comprises an inorganic material, e.g., an inorganic solid such as a silica, an alumina or a clay; or the solid support comprises an organic material, such as aluminum stearate.

The invention provides compositions having the formula:
(a) comprising the structure of any of the formulas described herein;
(b) comprising the structures of Formula 1, including Formula 1, 2, 2a, 2b, 2c, 3 and 4 structures:

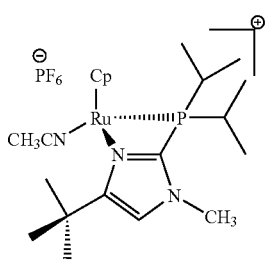

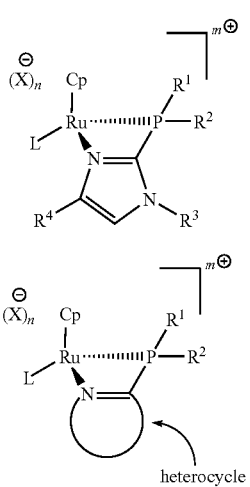

heterocycle

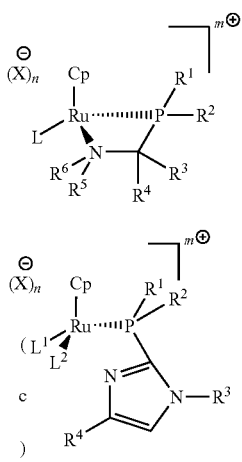

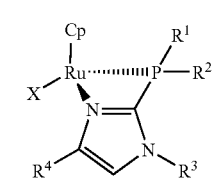

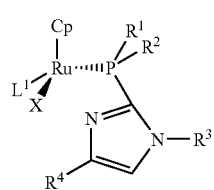

(c) the structure:

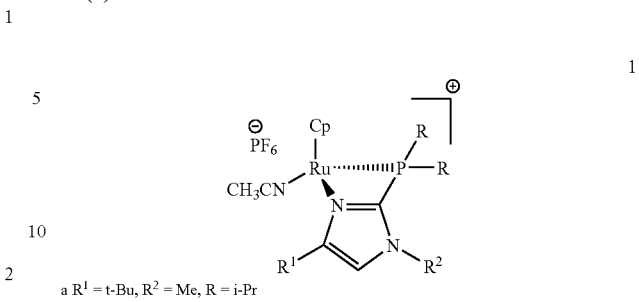

a $R^1$ = t-Bu, $R^2$ = Me, R = i-Pr wherein independently for (a), (b) and/or (c): $R^1$ is $CH_3CN$ or derivatives thereof, or a halide, a hydride, a carboxylate, a sulfonate, or any substituted derivatives thereof, or any neutral or anionic ligand;

$R^2$ is $CH_3CN$ or derivatives thereof, or a halide, a hydride, a carboxylate, a sulfonate, or any substituted derivatives thereof, or any neutral or anionic ligand;

and optionally the ruthenium is replaced (substituted) by a metal selected from the group consisting of a transition metal, a 1+, 2+, or 3+ oxidation state transition metal, a group 6, 7, 8, or 9 transition metal, chromium, molybdenum, tungsten, manganese, rhenium, iron, ruthenium, osmium, cobalt, rhodium, iridium, nickel, palladium, platinum, copper, silver and gold.

The invention provides alkene isomerization catalysts comprising the formula described herein (e.g., as described above).

The invention provides methods for alkene isomerization for converting a polyunsaturated organic molecule comprising two or more skipped (or non-conjugated) double bonds, to their conjugated isomers having conjugated double bonds, comprising (i) (a) providing the composition of the invention or the alkene isomerization catalyst of the invention, and (b) contacting the composition or alkene isomerization catalyst with the polyunsaturated organic molecule under conditions wherein the skipped (or non-conjugated) double bonds are isomerized to a conjugated double bond isomer form;

(ii) the method of (i), wherein the non-conjugated double bonds are separated by a methylene group, an ethylene group, a propylene or a longer group; or (iii) the method of (i) or (ii), wherein the polyunsaturated organic molecule comprises or is a triglyceride, fat, oil or derivative therefrom, or a fatty acid, or a polyunsaturated fatty acid, triglyceride, fat, oil or a derivative thereof.

In one embodiment of the methods of the invention, the polyunsaturated organic molecule or triglyceride, fat, oil or derivative or fatty acid comprises, or is derived from, linoleic acid, linseed, fish, soybean, tall, tung, corn, sunflower, safflower, castor and/or oiticica oil and/or fat. The polyunsaturated organic molecule or triglyceride, fat, oil or derivative therefrom can comprise, or can be derived from linoleic acid or methyl linoleate.

The invention provides methods for conjugating at least two double bonds in a non-conjugated double bond-comprising hydrocarbon substance (composition) or polymer to generate a conjugated isomer thereof having conjugated double bonds (e.g., conjugating two, some or all of the double bonds), comprising (i) (a) providing the composition of the invention or the alkene isomerization catalyst of the invention, and (b) contacting the non-conjugated double bond-comprising composition with the composition or alkene isomerization catalyst of (a) under conditions wherein two or several of the skipped (or non-conjugated) double bonds are isomerized to a conjugated double bond isomer form;

(ii) the method of (i), wherein the non-conjugated double bonds are separated by a methylene group, an ethylene group, a propylene or a longer group;

(iii) the method of (i) or (ii), wherein all the non-conjugated double bonds are conjugated in the isomer; or (iv) the method of any of (i) to (iii), wherein the double bond-comprising hydrocarbon substance or polymer comprises or is a polyunsaturated organic molecule, a triglyceride, fat, oil or derivative therefrom, or a fatty acid, or a polyunsaturated fatty acid, triglyceride, fat, oil or a derivative thereof.

In one embodiment of the methods of the invention, the reaction conditions comprise anywhere between about 0.01 mol % catalyst and 10 mol % catalyst, or between about 0.5 mol % catalyst and 1.0 mol % catalyst, or between about 1.0 mol % catalyst and 5.0 mol % catalyst, or 1, 2, 3, 4, 5, 6, 7, 8, 9 or 10 or more mol % catalyst, or about 2.4 mol % catalyst.

In one embodiment of the methods of the invention, the reaction conditions comprise a temperature in a range from about 60° C. to about 80° C., or a temperature at about 65° C., 66° C., 67° C., 68° C., 69° C., 70° C., 71° C., 72° C., 73° C., 74° C. or 75° C. or more. The reaction conditions can comprise an oxygen-free environment. The oxygen-free environment can comprise use of an oxygen-free acetone, and the catalyst is dissolved in the acetone.

The invention provides methods for making a conjugated linoleic acid or methyl linoleate comprising use of the composition of the invention, or the alkene isomerization catalyst of the invention, as a catalyst for conjugating double bonds.

The invention provides methods for converting an imidazole with one nitrogen unsubstituted to a salt, and for isomerizing alkenes comprising the following protocol ("Scheme 1"):

Synthesis of solid-phase catalyst:

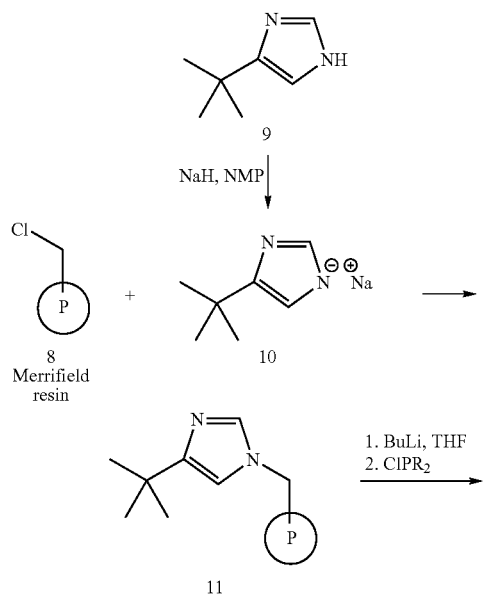

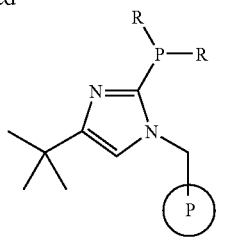

12
a R = i-Pr
b R = Ph 7,
acetone

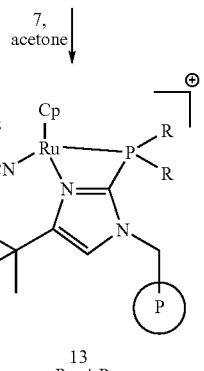

13
a R = i-Pr
b R = Ph

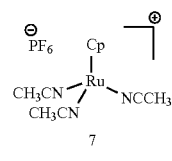

7

In one embodiment, the methods comprise converting 4(5)-tert-butylimidazole (compound 9) to its sodium salt (compound 10), and displacing a benzylic chloride on Merrifield resin (8) to produce an imidazolyl resin (compound 11).

In one embodiment, the methods comprise (a) converting a polymer, nanoparticle or microsphere, or solid support to a composition comprising a phosphine containing an acidic or basic group; or (b) the method of (a), wherein the phosphine is or comprises a heterocyclic phosphine.

The invention provides catalysts for alkene isomerization immobilized on a solid or semi-solid support comprising (a) (i) a catalyst for alkene isomerization having a formula as set forth in claim 1, or having the formula of compound 13a or compound 13b of Scheme 1 as described herein, or equivalents thereof, and (ii) a solid or semi-solid support, wherein the catalyst is immobilized on the solid or semi-solid support; or (b) the catalyst of (a), wherein the solid or semi-solid support is a resin-based support, or a gel support, or a nanoparticle or microsphere.

The invention provides methods for the isomerization of diallyl ether by —P(i-Pr)₂ catalyst 13a (Scheme 1 as described herein) comprising:

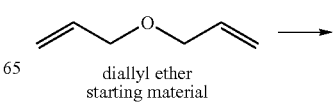

diallyl ether
starting material

-continued

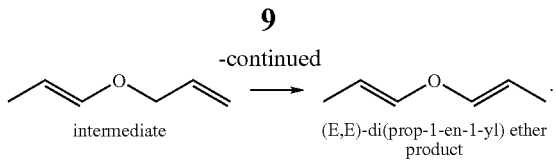

intermediate → (E,E)-di(prop-1-en-1-yl) ether product

The invention provides methods for making an imidazolylphosphine or other heterocyclic phosphine ligand attached to a solid support, comprising the following scheme:

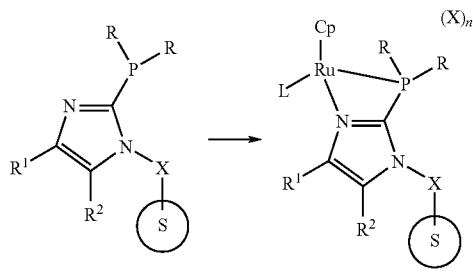

wherein X is one or more atom(s) used for covalent attachment to solid support S, L is or comprises $CH_3CN$ or derivatives thereof, halide, hydride, carboxylate, sulfonate, or any substituted derivatives thereof, or any neutral or anionic ligand, and R is or comprises $CH(CH_3)_2$, $C(CH_3)_2$, or any alkyl or aryl group, or a heteroaryl group, and $R^1$, $R^2$ can be independently $CH(CH_3)_2$, $C(CH_3)_2$, or any alkyl or aryl group, or a heteroaryl group, or hydrogen. In one embodiment, X is/are sufficient anion(s) to balance charge, or X is or comprises $PF_6$, halide, or carboxylate, sulfonate, tetraalkyl- or tetraphenylborate, or any substituted derivatives thereof.

The invention provides methods for the isomerization of 4-allylanisole by —P(i-Pr)$_2$ catalyst 13a (Scheme 1 as described herein) comprising:

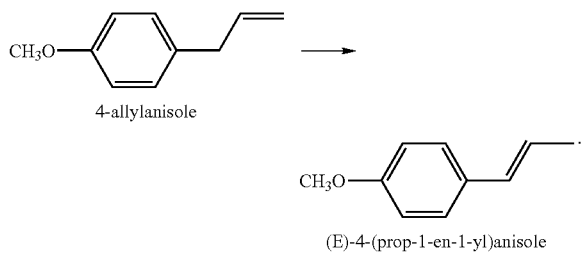

The invention provides products of manufacture comprising: a composition of invention, the alkene isomerization catalyst of the invention, or an immobilized catalyst of the invention, or a combination thereof.

The invention provides kits comprising: a composition of invention, the alkene isomerization catalyst of the invention, or an immobilized catalyst of the invention, or a combination thereof.

The invention provides formulations, e.g., liquid, semisolid or gel formulations, comprising: a composition of invention, the alkene isomerization catalyst of the invention, or an immobilized catalyst of the invention, or a combination thereof.

The invention provides resins or solid or semisolid (e.g., gel) supports, comprising (a) a composition of invention, the alkene isomerization catalyst of the invention, or an immobilized catalyst of the invention, or a combination thereof; or (b) the resin of (a), wherein the resin is or comprises a cellulose resin, a ethylsulfoxycellulose, a carboxymethyl cellulose or a hydroxyethyl cellulose resin, a fluorine-containing resin, a polymeric resin, urethane resin, an epoxy resin, a polyester resin, a phenol resin, a melamine resin, and/or a silicone resin; or (c) the solid or semisolid support of (a) comprising or consisting of an inorganic material, an inorganic solid, a silica, an alumina or a clay; or an organic material, or an aluminum stearate; or (d) the solid or semisolid support of (a) comprising or consisting of a nanoparticle or microsphere.

The invention provides compositions comprising (i) (a) a polyunsaturated organic molecule; and (b) a composition of invention, the alkene isomerization catalyst of the invention, or an immobilized catalyst of the invention, or a combination thereof; or (ii) the composition of (a), wherein the polyunsaturated organic molecule is or comprises a triglyceride, a fat, an oil, a fatty acid, a linoleic acid, a linseed oil, fish oil and/or fat, soybean oil and/or fat, tung oil and/or fat, corn oil and/or fat, sunflower oil and/or fat, safflower oil and/or fat, castor oil and/or fat and/or an oiticica oil and/or a fat.

The details of one or more embodiments of the invention are set forth in the accompanying drawings and the description below. Other features, objects, and advantages of the invention will be apparent from the description and drawings, and from the claims.

All publications, patents and patent applications cited herein are hereby expressly incorporated by reference for all purposes.

DETAILED DESCRIPTION OF THE INVENTION

The invention provides ruthenium-comprising catalysts, and methods of making and using them, for conjugating or isomerizing double bonds in polyunsaturated hydrocarbons, including polyunsaturated fatty acid derivatives, such as natural fats and oils, where the polyunsaturated hydrocarbons comprise (contain) more than one carbon to carbon double bond (e.g., two, 3, 4, 5, 6, 7, or more double bonds)—where in one aspect the double bonds are separated by a methylene group (so-called "methylene interrupted" double bonds); and in another aspect are separated by a group comprising two or more carbons, such as ethylene or propylene groups (the term "conjugating" as used herein describes making triglycerides, fats and oils which have double bonds on adjacent carbon atoms).

Thus, in one aspect the invention provides compositions (as catalysts) and methods for treating (processing) fats and oils comprising "interrupted" double bonds, including "methylene-, ethylene- or propylene-interrupted" double bonds, to generate isomers with "conjugated" double bonds.

The fats and oils generated using the compositions (e.g., catalysts) and methods of the invention can be used in polymerization applications, including industrial polymerization applications, to make coatings, adhesives and the like. In some aspects, conjugated fats and oils generated using the compositions (e.g., catalysts) and methods of the invention have better drying qualities, for example, oils generated practicing the compositions or methods of this invention have improved drying qualities to make improved bonding systems for various wood and fiber products. Some examples of such "drying oils" that can be treated by practicing the compositions (e.g., catalysts) and methods of the invention are: linseed, fish, soybean, tall, tung, castor and oiticica. Thus, in alternative aspects, compositions (e.g., catalysts) and methods of the invention are used to generate fatty acid derivatives, including conjugated double bond-comprising fats and oils, for bonding various wood, wood chips, fibers and composites materials, and to make improved oriented strand boards ("OSB"), particle boards, plywood and the like.

Compositions (e.g., catalysts) and methods of the invention also can be used to generate adhesives as bonding systems for wood composite products. Composites made from wood fibers, chips and fillers can be bonded using conjugated double bond-comprising fats and oils made by the methods and catalysts of this invention in place of, or in addition to, phenolic resins, polymeric methylene diphenyl diisocyanates, protein glues, and the like. In one aspect, when OSB or particle board is made, the wood and adhesive (comprising conjugated isomers the invention) are placed in a press which applies heat and pressure, the temperature, time and pressure each being a function of the composite being produced.

Drying oils that can be treated using the compositions (e.g., catalysts) and methods of the invention include fatty acids having a plurality of (e.g., two or three) double bonds. In one aspect, the one methylene interrupted fatty acid oils treated by the compositions and methods of this invention include: linseed, fish, soybean, tall, tung, corn, sunflower, safflower, castor and/or oiticica oils and/or fats. The compositions and methods of this invention can be used to generate conjugated isomers of any vegetable oil or its derivative; for example, common modifications to which common vegetable oils may be subjected include interesterification, fractionation, winterization and the like. These are processes which modify the fatty acid distribution of the original oil. For example, palm oil may be subjected to fractionation in order to form a palm olein fraction; which may comprise non-conjugated double bond unsaturation which can be isomerized by practicing the compositions and methods of this invention.

A second use of the fats and oils generated using the compositions (e.g., catalysts) and methods of the invention are in formation of CLA (conjugated linoleic acid) derivatives which have been shown to have beneficial anti-cancer properties and are valued as an additive to foods such as milk and dairy products, potato chips, etc. CLA derivatives can be formed by metal catalysts from linoleic acid, as well as using enzymes.

A third use of the fats and oils generated using the compositions (e.g., catalysts) and methods of the invention are in processing these materials before their use in other industrial processes.

In one aspect, the catalysts of this invention can be prepared from phosphine ligands and a cyclopentadienyl metal complex.

In one aspect, fatty acid derivatives, including conjugated double bond-comprising fats and oils, processed (made, generated) by using the compositions and methods of this invention include (comprise) alkenol hydrocarbons having separated alkene and alcohol groups; a catalyst of the invention can move the double bond across numerous carbon atoms. In another aspect, the hydrocarbon processed by using the compositions and methods of this invention comprises (includes) achiral alkanols; and a catalyst of the invention can form a chiral alcohol. In another embodiment, deuterated water may be added to the isomerization reaction mixture for forming deuterated hydrocarbon species.

The catalysts of the invention can comprise use of a transition metal atom such as ruthenium surrounded by ligands. In alternative embodiments, for good (to enhance) catalytic performance, the invention incorporates use of ligands comprising (including) not only atom(s) to bind to the metal, but also atom(s) which can act as bases or acids. Without being held to any theory of these catalysts' (of the invention) actions, it is believed that the combined action of the transition metal and the bases or acids in the same molecule are what create the uniquely powerful and efficient catalysts for moving double bonds in organic molecules. Moreover, in alternative embodiments, these catalysts can be extremely selective, for example leaving the cis alkene of oleic acid derivatives unchanged or nearly so, under conditions where the skipped double bonds of polyunsaturated fats are brought into conjugation.

Catalysts of the invention can be prepared by various methods, e.g., as shown in Scheme I, by using a cyclopentadienyl-metal complex (CpM) and an imidazol-2-yl phosphine ligand to give the catalyst structure of Formula I.

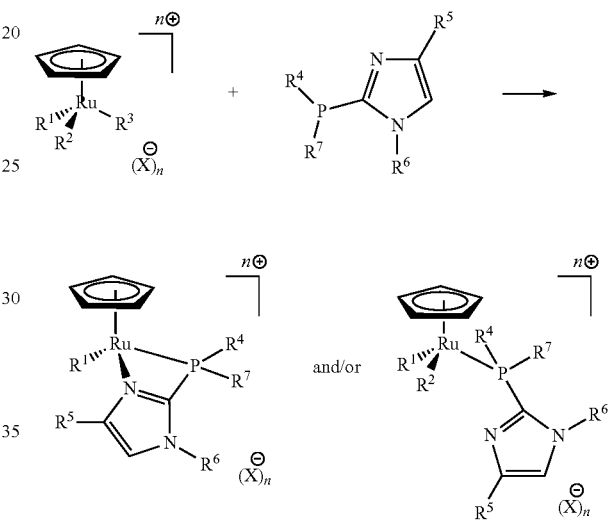

Scheme I $R^1$ can be $CH_3CN$ or derivatives thereof, halide, hydride, carboxylate, sulfonate, or any substituted derivatives thereof, or any neutral or anionic ligand.

$R^2$ can be $CH_3CN$ or derivatives thereof, halide, hydride, carboxylate, sulfonate, or any substituted derivatives thereof, or any neutral or anionic ligand.

$R^3$ can be $CH_3CN$ or derivatives thereof, halide, hydride, carboxylate, sulfonate, or any substituted derivatives thereof, or any neutral or anionic ligand.

$R^4$ can be $CH(CH_3)_2$, $C(CH_3)_2$, or any alkyl or aryl group, including heteroaryl.

$R^5$ can be $C(CH_3)_3$, H, $CH(CH_3)_2$, or any alkyl or aryl group, including heteroaryl.

$R^6$ can be $CH_3$, H, or any alkyl or aryl group.

$R^7$ can be $CH(CH_3)_2$, $C(CH_3)_2$, or any alkyl or aryl group, including heteroaryl.

M can be a transition metal, a 1+, 2+, or 3+ oxidation state transition metal, a group 6, 7, 8, or 9 transition metal, chromium, molybdenum, tungsten, manganese, rhenium, iron, ruthenium, osmium, cobalt, rhodium, iridium, nickel, palladium, platinum, copper, silver, or gold.

n can be 0, 1, 2, 3, 4, 5, 6, 7 or 8 or more.

In $(X)_n$ the "n" can be 1, 2, 3, 4, 5, 6, 7, or more, e.g., $(X)_n$ can be $PF_6$.

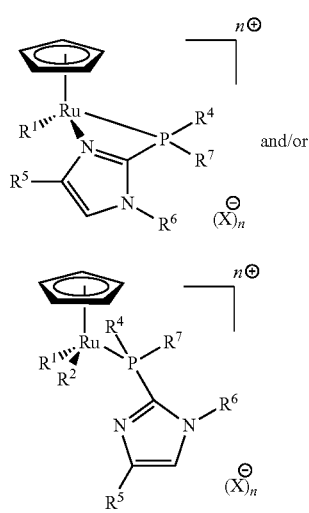

Formula I and/or

Formula VII

By using an alternative ligand, an exemplary catalyst of the invention can be prepared as shown in Scheme II to get the structure of Formula II.

Scheme II

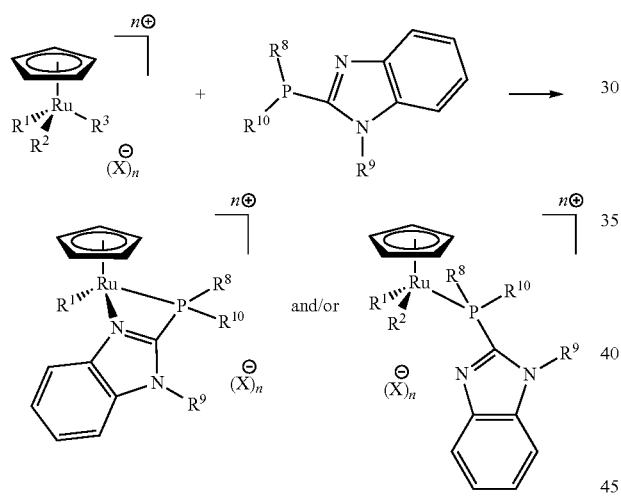

wherein $R^8$ can be $CH(CH_3)_2$, $C(CH_3)_3$, or any alkyl or aryl group, including heteroaryl.

$R^9$ can be $CH_3$, H, or any alkyl or aryl group.

$R^{10}$ can be $CH(CH_3)_2$, $C(CH_3)_3$, or any alkyl or aryl group, including heteroaryl.

Formula II

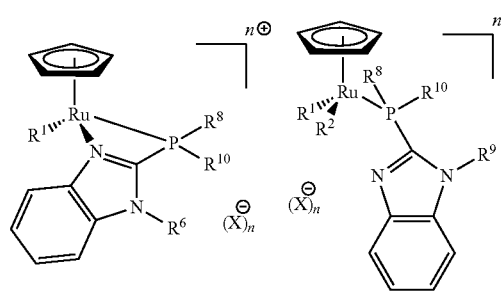

Scheme III shows an exemplary synthesis of a catalyst of this invention by using a CpM and a pyrid-2-yl phosphine ligand to give the exemplary catalyst structure of Formula III.

Scheme III

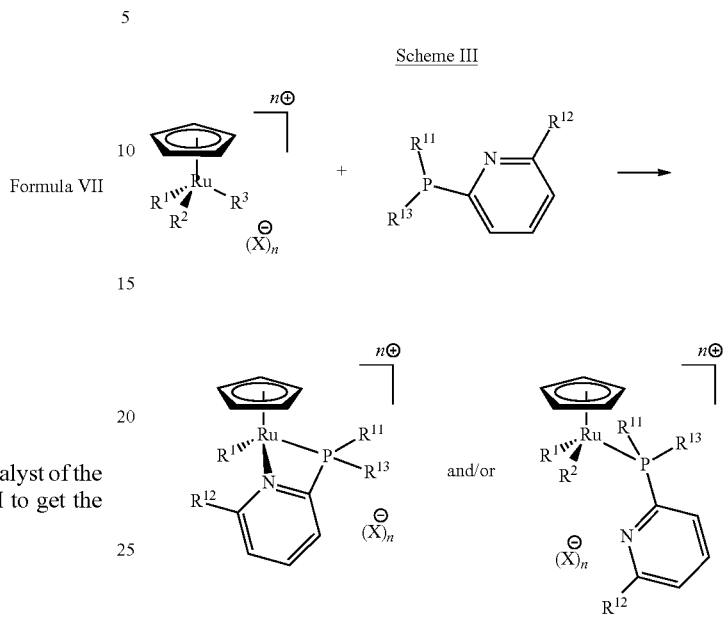

wherein $R^{11}$ can be $CH(CH_3)_2$, $C(CH_3)_3$, or any alkyl or aryl group, including heteroaryl.

$R^{12}$ can be $CH(CH_3)_2$, $C(CH_3)_3$, or any alkyl or aryl group, including heteroaryl.

$R^{13}$ can be $CH(CH_3)_2$, $C(CH_3)_3$, or any alkyl or aryl group, including heteroaryl.

Formula III

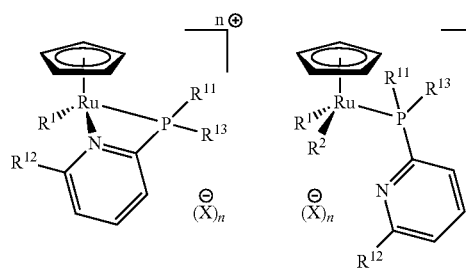

Scheme IIIA shows an exemplary synthesis of a catalyst of this invention by using a CpM and an aminoalkylphosphine ligand to give the exemplary catalyst structure of Formula IIIA.

Scheme IIIA

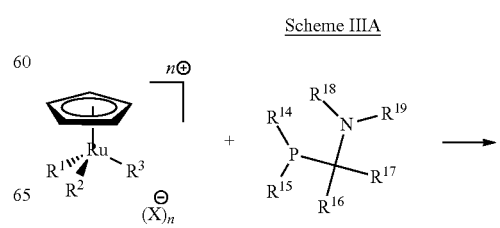

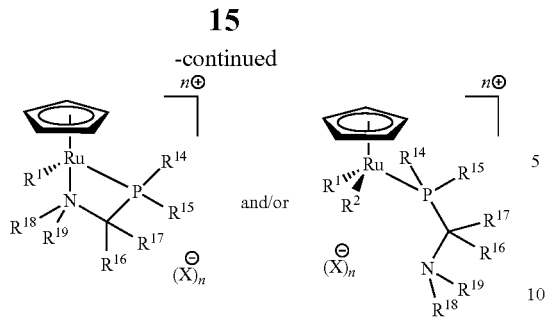

wherein $R^{14}$ can be $CH(CH_3)_2$, $C(CH_3)_3$, or any alkyl or aryl group, including heteroaryl.

$R^{15}$ can be $CH(CH_3)_2$, $C(CH_3)_3$, or any alkyl or aryl group, including heteroaryl.

$R^{16}$ can be $CH(CH_3)_2$, $C(CH_3)_3$, or any alkyl or aryl group, including heteroaryl, or hydrogen.

$R^{17}$ can be $CH(CH_3)_2$, $C(CH_3)_3$, or any alkyl or aryl group, including heteroaryl, or hydrogen.

$R^{18}$ can be $CH(CH_3)_2$, $C(CH_3)_3$, or any alkyl or aryl group, including heteroaryl.

$R^{19}$ can be $CH(CH_3)_2$, $C(CH_3)_3$, or any alkyl or aryl group, including heteroaryl Formula IIIA

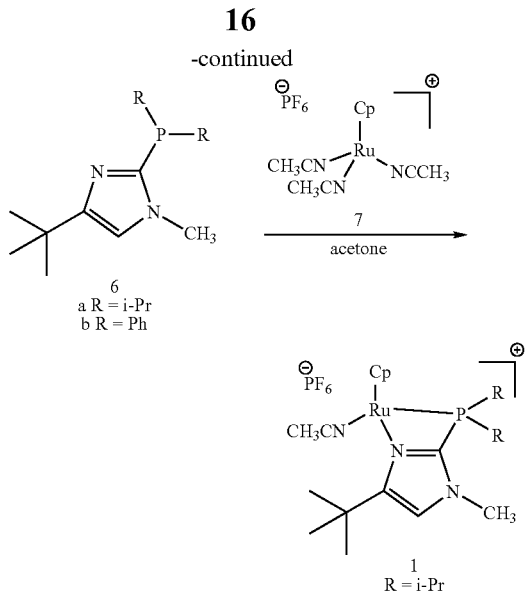

In addition, in alternative embodiments, the Cp ligand ($C_5H_5$) in Formulas I, II, III and IIIA can be substituted with any alkyl or aryl group or groups, including heteroaryl, or any other substituents. In alternative embodiments, the Cp ligand could be replaced with ligands such as indenyl or benzene or any of its derivatives (substituted with any alkyl or aryl group or groups, including heteroaryl, or any other substituents), Tp (tris-pyrazolylborate) or any of its derivatives (substituted with any alkyl or aryl group or groups, including heteroaryl, or any other substituents), or any ligand of similar structure capable of providing an active catalyst.

Heterocyclic Resin-Based Compositions

The invention provides heterocyclic resin-based compositions, and methods of using them, for making catalysts for alkene isomerization and exchange of hydrogens for deuterium or tritium isotopes.

Synthesis of polymer-supported catalyst - Scheme 1

Synthesis of solution-phase catalyst:

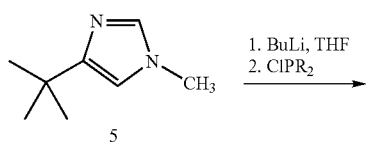

Synthesis of solid-phase catalyst:

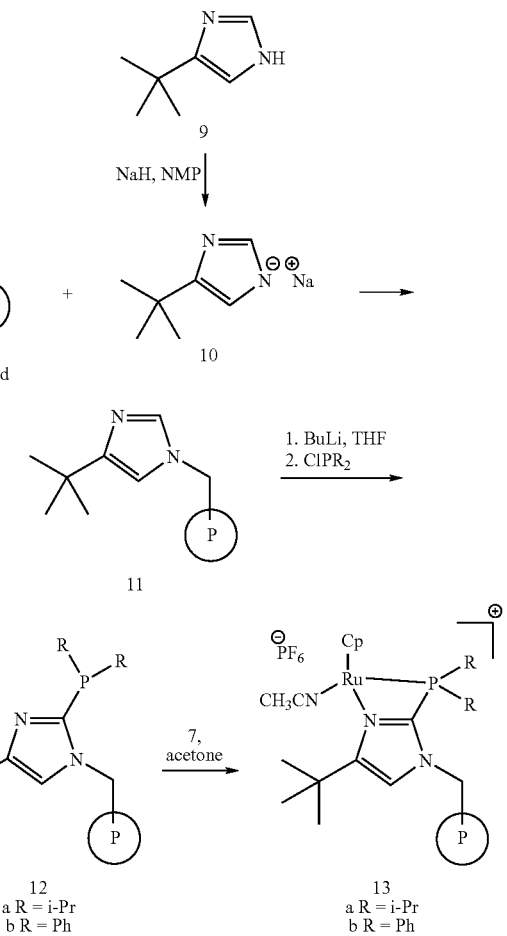

The inventors have previously reported soluble compound I as an extremely active and highly selective catalyst for alkene isomerization (*J. Am. Chem. Soc.* 2007, 129, 9592-9593) as well as deuteration. The synthesis of 1 is described in the published reference *J. Am. Chem. Soc.* 2007, 129, 9592-9593. The syntheses of ligands 6a and 6b starting with 5 are described in (respectively) *J. Am. Chem. Soc.* 2006, 128, 438-453 and *Angew. Chem., Int. Ed.* 2001, 40, 3884-3887.

Catalyst preparation: In this embodiment of the invention, 4(5)-tert-butylimidazole (9) was converted to its sodium salt (10) and displace the benzylic chloride on Merrifield resin (8) to produce imidazolyl resin 11. Model solution-phase studies with iodomethane or benzylic halides showed that the alkylation of 10 occurs at the nitrogen shown with at least 90-95% selectivity. Here, we subjected a sample of 11 to combustion analysis for C, H and N to show that the expected level of nitrogen was present in the resin. The imidazolyl resin was then converted either to 12a or 12b and then to 13a or 13b. Both resins showed activity for alkene isomerization but 13a was faster.

Results: both catalysts work, but 13a is somewhat faster. Isomerization of 4-allylanisole with 2 mol % catalyst 13a is complete in 1 h at RT, giving exclusively (E)-isomer, whereas 13b requires 2 h. The (E)-isomer product is stable to both catalysts after 100 h additional exposure, showing the same very high kinetic selectivity shown by solution-phase analog 1. Similarly, diallyl ether gives exclusively (E,E)-di(prop-1-en-1-yl)ether. From the data obtained so far, 13a appears to be about 10-20 times slower than 1 at the same catalyst loading, in same solvent (acetone), same substrate concentration (0.5 M), and at the same temperature (ambient).

Additional embodiments: Using the novel methods of this invention (e.g., the chemistry shown for converting 8 to 11), any imidazole derivative or heterocycle capable of displacing the chloride in 8 can be used to practice this invention.

Imidazole derivatives can be used to practice this invention, including benzimidazole or other annelated imidazoles. Other heterocycles that can be used in practicing this invention include indole, pyrrole, and equivalents, and the like. Other resins also can be used.

In another aspect, the methods of the invention provide reacting analogs of 11 with the appropriate base followed by an appropriate phosphine derivative to generate analogs of 12.

In another aspect of the invention, the methods comprise adding any number of metal complexes to analogs of 12 to generate analogs of 13.

Conversion of Merrifield Resin 8 to Imidazolyl Resin 11

The resin used was MERRIFIELD VHL™ (50-100 mesh) (Novabiochem, Merck KGaA, Darmstadt, Germany) for which the content of reactive chloromethyl groups was assayed at 1.7 mmol per g. In the glovebox, sodium hydride (124.1 mg, 60% in mineral oil, 3.10 mmol) in a vial was rinsed with dry hexanes, and the solid was dried in the glovebox. A solution of 4(5)-tert-butylimidazole (365.6 mg, 3.26 mmol) in dry NMP (1 mL) was added to the sodium hydride, causing foaming. Additional dry NMP (total 1 mL in two portions) was used to rinse the residual 4(5)-tert-butylimidazole solution into the reaction mixture. After 15 min, the reaction solution was transferred to a vial containing resin (1.003 g, 1.7 mequiv/g), which swelled, so additional NMP (total 6 mL) was added. The mixture was heated in an oil bath at 50° C. for 22 h before being allowed to cool and transferred to a polyethylene syringe with fitted disk. The liquid was expelled and the resin rinsed with NMP (total 20 mL, in four portions), methanol, then alternating between methanol and $CH_2Cl_2$ (four times each). In the syringe the resin was stirred with $CH_2Cl_2$ for 1 h before draining the liquid and storing the resin under oil-pump vacuum for 22 h. At that point the mass of resin was 1.1757 g. A 23-mg sample was removed, and both this sample and the bulk resin were stored under oil-pump vacuum an additional 10 days, leaving 1.0836 g in the syringe. Elemental analysis of the smaller sample—Found: C, 87.17; H, 7.80; N, 5.00.

If starting resin contains 1.7 mmol per g reactive chloromethyl groups, then there is 60.3 mg Cl per g and 939.7 mg other material. If all of the Cl atoms are substituted by tert-butylimidazolyl groups then the expected mass of product resin would be 939.7+189.0 mg=1.1287 g, compared with 1.106 g. Assuming 100% yield of substitution, there are 1.7 mmol/1.106 g=1.536 meq per g imidazolyl groups in the product.

Analysis of 5.00% N in product resin means 50.0 mg N per g product=3.57 mmol per g, but there are two N in imidazole, so therefore by N analysis there are 1.78 mmol imidazole per g, assuming that no NMP remains in the resin.

Synthesis of —P(i-Pr)$_2$ Resin 12a

In the glovebox, dry THF (3 mL) was added to resin (227.3 mg, 0.349 mmol) and a stir bar in a 10 mL polyethylene syringe with fitted disk and TEFLON™ (DuPont, Wilmington, Del.) stopcock assembly. After 2 h, the syringe plunger was removed and the contents of the syringe stirred. BuLi (0.370 mL, 1.49 M in hexanes, 0.55 mmol, 1.58 equiv) was added over 1 min to the stirred contents. The resin became reddish orange. After 7 min, the liquid was drained, and the resin washed with dry THF (2×2 mL). A solution of ClP(i-Pr$_2$)$_2$ (81.6 mg, 0.535 mmol, 1.53 equiv) in dry THF (1 mL) was added and the color of the resin changed to yellow almost immediately. After 40 min, the liquid was drained and the resin washed with THF (3×2 mL). The stir bar was removed and the syringe placed under vacuum for 3 d, leaving 272.2 mg. (The expected mass gain would be 0.349 mmol× 117.14=40.9 mg, cf. 44.9 mg observed.)

Synthesis of —P(i-Pr)$_2$ Catalyst 13a

To the resin from the previous section was added acetone (2 mL). After 15 min, a solution of CpRu(CH$_3$CN)$_3$ PF$_6$ (191.8 mg, 0.442 mmol, 1.27 equiv) in acetone (2 mL) was added. The resin turned a dark brown color. To the vial used to make the solution of ruthenium complex was added acetone (2 mL) and this solution was added to the resin reaction mixture. Over the next 1 h, the contents of the syringe were agitated occasionally. The liquid was drained and the resin rinsed with acetone (6×2 mL) before being stored under oil pump vacuum for 3.5 d, leaving 375.1 mg. (Assuming binding of CpRu (CH$_3$CN) to the resin along with the PF$_6$ counterion, the expected mass gain would be 0.349 mmol×352.20=122.9 mg, cf. 102.9 mg observed. For the purposes of calculating the concentration of reactive catalyst, 100% yields and purity were assumed, leading the a calculation of 0.349 mmol/ 0.3751 g=0.93 mmol active catalyst per g.)

Synthesis of —PPh$_2$ Resin 12b

In the glovebox, dry THF (3 mL) was added to imidazolyl resin (169.0 mg, 0.260 mmol) and a stir bar in a 10 mL polyethylene syringe with fritted disk and Teflon stopcock assembly. After 2 h, the syringe plunger was removed and the contents of the syringe stirred. BuLi (0.265 mL, 1.49 M in hexanes, 0.39 mmol, 1.5 equiv) was added over 1 min to the stirred contents. The resin became reddish orange. After 5 min, the liquid was drained, and the resin washed with dry THF (2×2 mL). A solution of ClPPh$_2$ (96.3 mg, 0.436 mmol, 1.68 equiv) in dry THF (1 mL) was added. The color of the resin changed to orangish yellow over the next 1 h. After 2 h, the liquid was drained and the resin washed with THF (3×2 mL). The stir bar was removed and the syringe placed under vacuum for 3 d, leaving 231.3 mg. (The expected mass gain would be 0.260 mmol×185.17=48.1 mg, cf. 62.3 mg observed.)

Synthesis of —PPh$_2$ Catalyst 13b

To the resin from the previous section was added acetone (2 mL). After 15 min, a solution of CpRu(CH$_3$CN)$_3$ PF$_6$ (144.5 mg, 0.333 mmol, 1.28 equiv) in acetone (2 mL) was added.

The resin turned a dark brown color. To the vial used to make the solution of ruthenium complex was added acetone (2 mL) and this solution was added to the resin reaction mixture. Over the next 1 h, the contents of the syringe were agitated occasionally. The liquid was drained and the resin rinsed with acetone (6×2 mL) before being stored under oil pump vacuum for 3.5 d, leaving 298.7 mg. (Assuming binding of CpRu (CH$_3$CN) to the resin along with the PF$_6$ counterion, the expected mass gain would be 0.260 mmol×352.20=91.6 mg, cf. 67.4 mg observed. For the purposes of calculating the concentration of reactive catalyst, 100% yields and purity were assumed, leading the a calculation of 0.260 mmol/ 0.2987 g=0.87 mmol active catalyst per g)

Use of the —P(i-Pr$_2$)$_2$ Catalyst 13a on 4-allylanisole

One scintillation vial was charged with catalyst (10.7 mg; assuming that the concentration of catalyst is 0.93 meq per g, 10.7 mg=0.010 mmol, 2 mol %) and a stir bar. A second vial was charged with 4-allylanisole (74.5 mg, 0.503 mmol) and internal standard (Me$_3$Si)$_4$C (0.3 mg) and the solids dissolved in acetone (0.43 mL). An aliquot (ca. 10 μL) of the solution was analyzed by $^1$H NMR by diluting it with acetone-d$_6$ (ca. 0.6 mL), using 10° pulses and 30 sec delays between acquisition cycles. The solution of 4-allylanisole and standard was transferred quantitatively to the catalyst vial using a pipet and additional acetone (0.50 mL, in two portions). The mixture was stirred gently. After 1 h and 100 h aliquots (ca. 20 μL) were removed for analysis by $^1$H NMR spectroscopy.

Use of the —PPh$_2$ Catalyst 13b on 4-allylanisole

One scintillation vial was charged with catalyst (11.6 mg; assuming that the concentration of catalyst is 0.87 meq per g, 11.6 mg=0.010 mmol, 2 mol %) and a stir bar. A second vial was charged with 4-allylanisole (74.8 mg, 0.505 mmol) and internal standard (Me$_3$Si)$_4$C (0.5 mg) and the solids dissolved in acetone (0.43 mL). An aliquot (ca. 10 μL) of the solution was analyzed by $^1$H NMR by diluting it with acetone-d$_6$ (ca. 0.6 mL), using 10° pulses and 30 sec delays between acquisition cycles. The solution of 4-allylanisole and standard was transferred quantitatively to the catalyst vial using a pipet and additional acetone (0.50 mL, in two portions). The mixture was stirred gently. After 1 h, 2 h, and 100 h aliquots (ca. 20 μL) were removed for analysis by $^1$H NMR spectroscopy.

Experiment 1

Isomerization of 4-allylanisole by —P(i-Pr)$_2$
Exemplary Catalyst of this Invention 13a

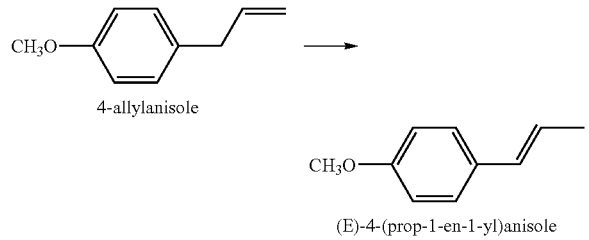

4-allylanisole (E)-4-(prop-1-en-1-yl)anisole

For 4-allylanisole: $^1$H NMR (600 MHz, acetone-d$_6$) δ 7.11 (~d, J≈8 Hz, 2H), 6.85 (~d, J≈8 Hz, 2H), 5.94 (tdd, J=6.7, 10.1, 17.0, 1H), 5.04 (~q of d, J≈2, =17.0, 1H), 4.99 (tdd, J=1.3, 2.2, 10.1, 1H), 3.76 (s, 3H), 3.31 (d, J=6.4 Hz, 2H).

For 4-(E-prop-1-en-1-yl)anisole: $^1$H NMR (400 MHz, acetone-d$_6$) δ 7.28 (~d, J≈9 Hz, 2H), 6.85 (~d, J≈9 Hz, 2H), 6.36 (qd, J=1.8, 15.7 Hz, 1H), 6.11 (qd, J=6.6, 15.7, 1H), 3.78 (s, 3H), 1.82 (dd, J=1.8, 6.6, 3H).

TABLE 1

Primary data (measured integrals in arbitrary units) and derived per cent starting material remaining and product yields.

| Compound(s)[a] | Chemical shifts of resonances (ppm) | Time | | |
|---|---|---|---|---|
| | | 0 h | 1 h | 100 h |
| sm + p | 3.76-3.80 (3H; all —OCH$_3$ peaks) | 167.83 | 156.62 | 167.98 |
| | units per proton for —OCH$_3$ peak(s) | 55.94 | 52.21 | 55.99 |
| sm | 7.11 | 110.84 | 0 | 0 |
| sm | 6.85 | 112.15 | [e] | [e] |
| sm | 5.94 | 55.53 | 0 | 0 |
| sm | 5.04 + 4.99 | 111.35 | 0 | 0 |
| sm | 3.31 | 110.70 | 0 | 0 |
| sm | units per proton[b] | 55.61 | 0 | 0 |
| sm | % starting material remaining[c] | 100 | 0 | 0 |
| p | 7.28 | 0 | 101.33 | 110.57 |
| p | 6.36 | 0 | 51.57 | 54.92 |
| p | 6.11 | 0 | 51.82 | 55.06 |
| p | 1.82 | 0 | 156.52 | 163.46 |
| p | units per proton[b] | 0 | 51.61 | 54.86 |
| p | % yield of product[d] | 0 | 98.9 | 98.0 |

[a]"Sm" and "p" mean starting material and product, respectively.
[b]Calculated by taking the average of integrations of the specified resonances.
[c]Calculated by dividing units per proton of starting material at time indicated by units per proton value for —OCH$_3$ peak(s).
[d]Calculated by dividing units per proton of product at time indicated by the units per proton value for —OCH$_3$ peak(s).
[e]Resonance for product appears at same chemical shift.

Experiment 2

Isomerization of 4-allylanisole by —PPh$_2$
Exemplary Catalyst of this Invention 13b

TABLE 2

Primary data (measured integrals in arbitrary units) and derived percent starting material remaining and product yields.

| Compound(s)[a] | Chemical shifts of resonances | Time | | | |
|---|---|---|---|---|---|
| | | 0 h | 1 h | 2 h | 100 h |
| sm + p | 3.76-3.80 (3H; all —OCH$_3$ peaks) | 340.58 | 338.82 | 342.24 | 373.02 |
| | units per proton for —OCH$_3$ peak(s) | 113.53 | 112.94 | 114.08 | 124.34 |
| sm | 7.11 | 224.83 | 9.92 | 0 | 0 |
| sm | 6.85 | 227.82 | [e] | [e] | [e] |
| sm | 5.94 | 110.06 | 6.39 | 0 | 0 |
| sm | 5.04 + 4.99 | 226.41 | 11.02 | 0 | 0 |
| sm | 3.31 | 225.74 | [f] | [f] | 0 |
| sm | units per proton[b] | 112.76 | 5.47 | 0 | 0 |
| sm | % starting material remaining[c] | 100 | 4.8 | 0 | 0 |
| p | 7.28 | 0 | 214.82 | 220.37 | 246.02 |
| p | 6.36 | 0 | 108.19 | 114.26 | 122.23 |
| p | 6.11 | 0 | 107.82 | 115.09 | 122.40 |
| p | 1.82 | 0 | 318.85 | 325.58 | 366.36 |
| p | units per proton[b] | 0 | 107.1 | 110.76 | 122.43 |
| p | % yield of product[d] | 0 | 94.8 | 97.1 | 98.5 |

[a] "Sm" and "p" mean starting material and product, respectively.
[b] Calculated by taking the average of integrations of the specified resonances.
[c] Calculated by dividing units per proton of starting material at time indicated by units per proton value for —OCH$_3$ peak(s).
[d] Calculated by dividing units per proton of product at time indicated by the units per proton value for —OCH$_3$ peak(s).
[e] Resonance for product appears at same chemical shift.
[f] Overlap with another unidentified peak precluded using this value.

Experiment 3

Isomerization of Diallyl Ether by —P(i-Pr)$_2$ Exemplary Catalyst of this Invention 13a

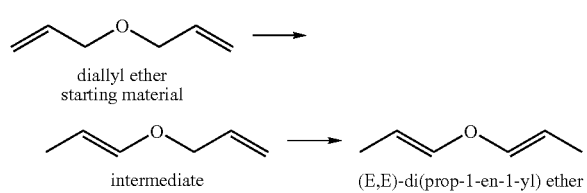

diallyl ether starting material intermediate → (E,E)-di(prop-1-en-1-yl) ether product For intermediate: $^1$H NMR (600 MHz, acetone-d$_6$) δ 6.23 (qd, J=1.7, 12.5), 5.91 (tdd, J=5.3, 10.5, 17.2, 1H), 5.27 (~q of d, J≈1.7, 17.2, 1H), 5.14 (~q of d, J≈1.6, 10.5, 1H), 4.76 (qd, J=6.7, 12.3, 1H), 4.16 (td, J=1.5, 5.2, 2H), 1.51 (dd, J=1.6, 6.7, 3H).

For product: $^1$H NMR (600 MHz, acetone-d$_6$) δ 6.29 (qd, J=1.7, 12.3), 4.99 (qd, J=6.8, 12.1, 2H), 1.54 (dd, J=1.7, 7.0, 6H).

TABLE 3

Primary data (measured integrals in arbitrary units) and derived percent starting material remaining and product yields.

| Com-pound(s)[a] | Chemical shifts of resonances | 0 h | 1 h | 8 h | 27 h |
|---|---|---|---|---|---|
| sm | 5.90 (2H) | 109.61 | [e] | [e] | [e] |
| sm | 5.25 (2H) | 108.73 | [e] | [e] | [e] |
| sm | 5.12 (2H) | 113.17 | 6.18 | 0 | 0 |
| sm | 3.95 (4H) | 223.36 | 10.70 | 0 | 0 |
| sm | units per proton[b] | 55.49 | 2.81 | 0 | 0 |
| sm | % starting material remaining[c] | 100 | 5.1 | 0 | 0 |
| i | 6.23 (1H) | 0 | 36.18 | 9.55 | 1.92 |
| i | 5.14 (1H) | 0 | 36.01 | 8.97 | 1.87 |
| i | 4.76 (1H) | 0 | 36.02 | 9.01 | 1.65 |
| i | 4.16 (2H) | 0 | 72.75 | 17.18 | 2.98 |
| i | 1.51 (3H) | 0 | 108.09 | 27.21 | 10.54[f] |
| i | units per proton[b] | 0 | 36.13 | 8.99 | 1.68 |
| i | % yield of intermediate[d] | 0 | 65.1 | 16.2 | 3.0 |
| p | 6.29 (2H) | 0 | 19.56 | 83.94 | 94.81 |
| p | 4.99 (2H) | 0 | 20.64 | 83.88 | 94.66 |
| p | 1.54 (6H) | 0 | 60.44 | 254.20 | 283.00 |
| p | units per proton[b] | 0 | 10.06 | 42.20 | 47.25 |
| p | % yield of product[d] | 0 | 18.1 | 76.1 | 85.1 |

[a] "Sm,", "i," and "p" mean starting material, intermediate and product, respectively.
[b] Calculated by taking the average of integrations of the specified resonances.
[c] Calculated by dividing units per proton of starting material at time indicated by units per proton value at time 0 h.
[d] Calculated by dividing units per proton of intermediate or product at time indicated by the units per proton value for starting material at time 0 h.
[e] Resonance for intermediate or product appears too close to allow separate integration.
[f] Proximity of large resonance at 1.54 precluded useful integration; this value not used in calculating yield.

Experiment 3A same as experiment 3, but run in a scintillation vial instead of conical vial. It appeared that because catalyst beads were more spread out in the vial, contact between reactant solution and beads was less effective; however, yields of intermediate and product at 1 and 8 h are similar.

TABLE 3A

Primary data (measured integrals in arbitrary units) and derived percent starting material remaining and product yields.

| Com-pound(s)[a] | Chemical shifts of resonances | 0 h | 1 h | 8 h |
|---|---|---|---|---|
| sm | 5.90 (2H) | 184.76 | [e] | [e] |
| sm | 5.25 (2H) | 188.16 | [e] | [e] |
| sm | 5.12 (2H) | 184.60 | 14.22 | 0 |
| sm | 3.95 (4H) | 368.53 | 24.51 | 0 |
| sm | units per proton[b] | 92.61 | 6.46 | 0 |
| sm | % starting material remaining[c] | 100 | 7.0 | 0 |
| i | 6.23 (1H) | 0 | 67.27 | 25.45 |
| i | 5.14 (1H) | 0 | 67.39 | 23.02 |
| i | 4.76 (1H) | 0 | 67.71 | 22.53 |
| i | 4.16 (2H) | 0 | 135.37 | 44.16 |
| i | 1.51 (3H) | 0 | 203.66 | 78.59 |
| i | units per proton[b] | 0 | 67.68 | 24.22 |
| i | % yield of intermediate[d] | 0 | 73.1 | 26.2 |
| p | 6.29 (2H) | 0 | 35.20 | 144.38 |
| p | 4.99 (2H) | 0 | 36.23 | 143.39 |
| p | 1.54 (6H) | 0 | 107.63 | 428.28 |
| p | units per proton[b] | 0 | 17.91 | 71.61 |
| p | % yield of product[d] | 0 | 19.3 | 77.3 |

[a] "Sm,", "i," and "p" mean starting material, intermediate and product, respectively.
[b] Calculated by taking the average of integrations of the specified resonances.
[c] Calculated by dividing units per proton of starting material at time indicated by units per proton value at time 0 h.
[d] Calculated by dividing units per proton of intermediate or product at time indicated by the units per proton value for starting material at time 0 h.
[e] Resonance for intermediate or product appears too close to allow separate integration.

Use of the —P(i-Pr$_2$)$_2$ Exemplary Catalyst of this Invention 13a in Deuterating and Isomerizing 4-allylanisole A conical vial was charged with catalyst (11.1 mg; assuming that the concentration of catalyst is 0.93 meq per g, 11.1 mg=0.010 mmol, 2 mol %) and a stir bar. Acetone-d$_6$ (0.50 mL) was added to allow the resin to swell. A scintillation vial was charged with 4-allylanisole (74.1 mg, 0.503 mmol) and D$_2$O (400.6 mg, 20.0 mmol), and acetone-d$_6$ (0.50 mL) was added. After allowing the resin to contact acetone for 10 min, transfer of the two-phase substrate/D$_2$O/acetone-d$_6$ mixture to the catalyst vial was begun. Transfer was completed using additional acetone-d$_6$ (0.50 mL, total three portions). The resulting homogeneous mixture was gently stirred for the first 4 h of reaction time.

The progress of the reaction was determined by periodic removal of an aliquot (ca. 0.1 mL) and dilution it with acetone-d$_6$ (ca. 0.6 mL). Analysis by $^1$H NMR used 10° pulses and 30 sec delays between acquisition cycles. The integral for the methoxy proton singlet was assigned a value of 3.00 units and all other integrals against that as internal standard.

The appearance of the peaks between 1.75 and 1.81 as observed at 600 MHz is consistent with the presence of the three expected product isotopomers which bear proton(s) at the methyl group. At 1.803 and 1.806 ppm are two peaks, assigned as the downfield pair of peaks in the dd for undeuterated product. The integral for these two peaks was doubled to give the values shown in Table 4 (non-boldface values). The upfield pair of peaks apparently overlap with the downfield portion of a seven-line pattern consistent with the monodeuterated methyl group (—CH$_2$D), where $^2J_{H-D} \approx {}^4J_{H-H}$=2.2 Hz and $^3J_{H-H}$=6.0 Hz. The integral for this seven-line pattern, distorted slightly at the downfield side by overlap with the two peaks mentioned above for undeuterated product, was measured and from that value was subtracted the contribution from the signal for undeuterated material. Finally, for dideuterated product (—CHD$_2$), a multiplet from 1.75 and perhaps overlapping with the upfield part of the pattern for monodeuterated product was seen.

The second set of values in Table 4 (in bold, after semicolons) were obtained from spectra in which the signal at 6.11 ppm was irradiated during the acquisition time, thus simplifying the signals near 1.80 ppm and allowing direct integration.

TABLE 4

Primary data (measured integrals, with those for the methoxy protons set to 3.00) and derived per cent starting material remaining and product yields.

| Compound(s)[a] | Chemical shifts of resonances (ppm) | Time | | |
|---|---|---|---|---|
| | | 1 h | 2 h | 48 h |
| p | 7.28 (2H) | 1.98 | 1.99 | 1.99 |
| p | 6.34 (1H) | 0.94 | 0.95 | 0.90 |
| p | 6.11 (1H) | 0.98 | 0.99 | 0.98 |
| p | 1.75-1.81 (3H) | 2.05 | 1.98 | 1.32 |
| p | —CH$_3$ units per proton | 0.58; 0.54[b] 0.18 | 0.56; 0.50[b] 0.17 | 0.18; 0.16[b] 0.05 |
| | —CH$_2$D units per proton | 1.38; 1.25[b] 0.63 | 1.31; 1.23[b] 0.62 | 0.78; 0.67[b] 0.34 |
| | —CHD$_2$ units per proton | 0.09; 0.12[b] 0.12 | 0.11; 0.16[b] 0.16 | 0.33; 0.38[b] 0.38 |
| | —CD$_3$ units per proton[c] | 0.03 | 0.05 | 0.23 |

[a]"p" means product. No starting material resonances visible even after only 1 h.
[b]See text above and the following: bold values are judged to be more reliable because irradiation at 6.11 ppm simplified the peaks between 1.75-1.81 ppm, allowing separate integrations of signals for —CH$_3$, —CH$_2$D, and —CHD$_2$ isotopomers (boldface values).
[c]Calculated by subtracting the units per proton values for the three observable isotopomers from 1.

Nanoparticles, Microspheres and Liposomes

The invention also provides nanoparticles, microspheres and liposomes comprising compounds, e.g., catalysts, of this invention. The compounds, e.g., catalysts, of this invention can be immobilized to (onto) the nanoparticle, microsphere or liposome, or alternatively, contained in (within) the nanoparticle, microsphere or liposome.

The invention also provides nanocells for immobilizing or sequestering a composition (e.g., a catalyst) of this invention. A nanocell can be formed by encapsulating a nanocore with a composition (e.g., a catalyst) of this invention; see, e.g., Sengupta, et al., U.S. Pat. Pub. No. 20050266067. The invention also provides multilayered liposomes comprising compounds of this invention, e.g., as described in Park, et al., U.S. Pat. Pub. No. 20070082042. Liposomes can be made using any method, e.g., as described in Park, et al., U.S. Pat. Pub. No. 20070042031. The invention also provides nanoparticles comprising compounds of this invention, as described, e.g., in U.S. Pat. Pub. No. 20070077286. Compounds of this invention can be fixed onto or contained within nanostructures, such as nanotubes, e.g., carbon nanotubes as described in U.S. Pat. No. 7,399,400; or nanoparticles as described in U.S. Pat. Nos. 7,384,545; 7,381,334; 7,368,295; 7,364,919 (describing nanoparticles comprising cores of metal atoms); U.S. Pat. No. 7,344,773 (describing uniformly distributed nanoparticles on monolayer films).

The compounds, e.g., catalysts, of this invention can be immobilized to (onto), or alternatively, contained in (within) any nanostructure, e.g., nanowires (see e.g., U.S. Pat. Nos. 6,872,645; 7,262,501) nanoporous silica, silicon nanowires, carbon nanotubes, carbon nanorods, or any conductive polymer.

Kits

The invention provides kits comprising compositions of this invention and instructions for practicing the methods of the invention.

The invention will be further described with reference to the following examples; however, it is to be understood that the invention is not limited to such examples.

Example 1

The following example describes an exemplary method for making an exemplary ruthenium-comprising catalyst composition of this invention.

In one embodiment, the CpM species comprises a transition metal that is preferably Ru(2+). The bifunctional catalysts, therefore, are prepared by reacting a precursor containing the cyclopentadienyl ligand and a ruthenium(2+) ion (CpRu+) with either an imidazol-2-yl or pyrid-2-yl phosphine ligand.

In Scheme IV there is provided an exemplary synthesis of an exemplary embodiment for the catalyst of Formula IV reacting CpRu and an imidazol-2-yl phosphine ligand.

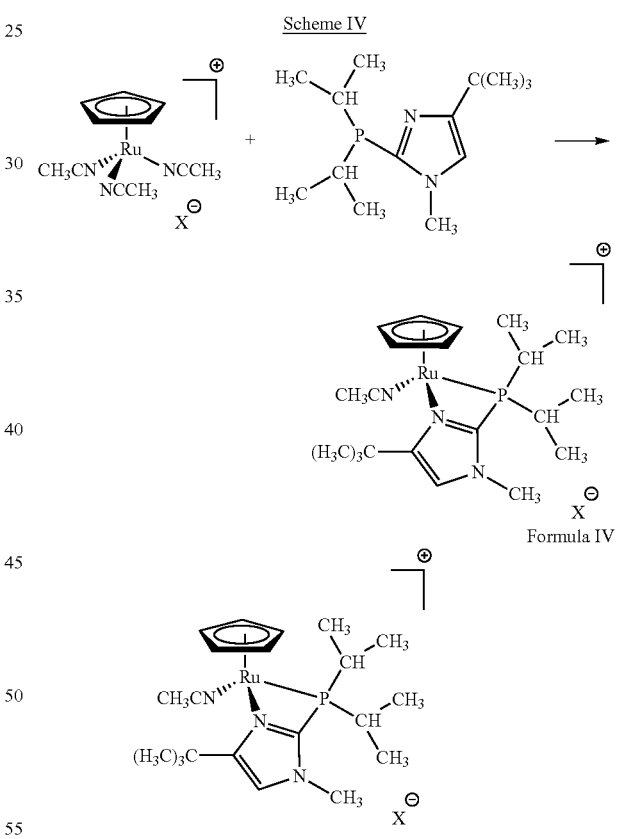

Scheme IV

Formula IV

Preparation of the Formula IV Catalyst [CpRu(η$^2$-P,N-L)(CH$_3$CN)]PF$_6$

[CpRu(CH$_3$CN)$_3$]PF$_6$ (296.9 mg, 0.68 mmol) was added to a scintillation vial containing a stir bar in the glove box. Dry, degassed CH$_2$Cl$_2$ (10 mL) was then added followed by the addition of the phosphine L (175.3 mg, 0.68 mmol). The mixture was allowed to stir overnight. The solvent was removed by vacuum, and to the residue was added pentane. Evaporation of solvents under vacuum led to brownish crystals. The solid was dissolved in CH$_2$Cl$_2$, followed by removal of the solvent under vacuum. This was repeated six times, until the amount of unchelated complex [CpRu($\eta^1$-P-L)(CH$_3$CN)](CH$_3$CN)$_2$]PF$_6$ was undetectable by NMR. This process yielded [CpRu($\eta^2$-P,N-L)(CH$_3$CN)]PF$_6$ (285 mg, 91% yield). $^1$H NMR (CDCl$_3$, 500 MHz) δ 1.01 (dd, 3H, J=7.5, 16.5 Hz), 1.208 (dd, 3H, J=10.5, 18 Hz), 1.26 (dd, 3H, obscured by s at 1.30), 1.30 (s, 9H), 1.45 (dd, 3H, J=6.5, 17 Hz), 2.30 (s, 3H), 2.57-2.63 (m, 1H), 2.83-2.88 (m, 1H), 3.66 (s, 3H), 4.64 (d, 5H, J=0.5 Hz), 6.66 (s, 1H). $^{31}$P NMR (CD$_3$COCD$_3$, 500 MHz) δ 39.43 (s).

Example 2

The following example describes an exemplary method for making an exemplary ruthenium-comprising catalyst composition of this invention.

Scheme V provides the synthesis of a further example of the invention bifunctional catalyst. The exemplary catalyst was synthesized under conditions similar those described above. The exemplary catalyst is illustrated in Formula V.

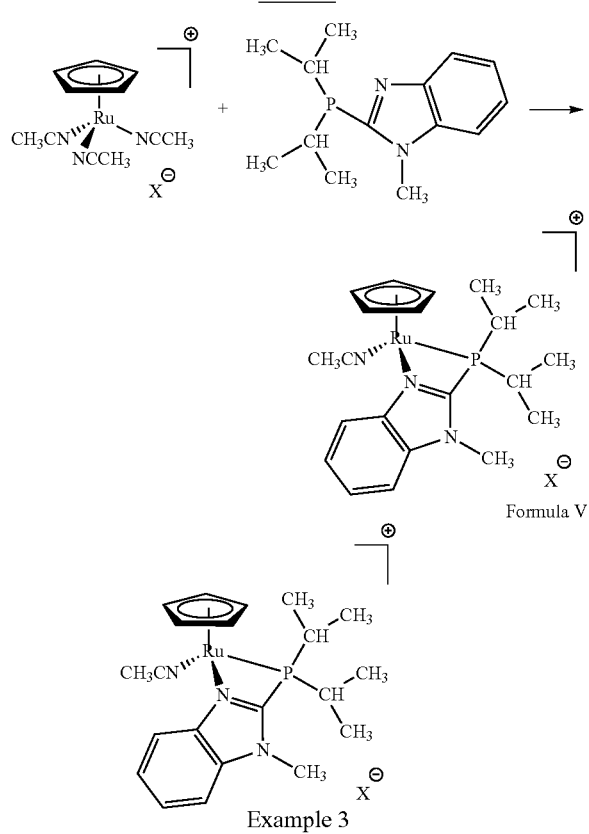

In alternative embodiments, these bifunctional catalysts of this invention, derived from reacting ligands and transition metals, are useful for forming isomers of unsaturated hydrocarbons, for forming chiral aldehydes from achiral alkenols, and for forming deuterated alkenes.

Example 4

Isomerization of Pent-4-en-1-ol to pentanal

The following example describes an exemplary method of this invention using an exemplary ruthenium-comprising catalyst composition of this invention.

This exemplary method of the invention uses an exemplary catalyst of the invention to isomerize pent-4-en-1-ol to pentanal, using the catalyst of Formula IV.

Scheme VI

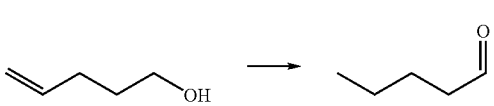

To a J. Young re-sealable NMR tube in the glovebox was added pent-4-en-1-ol (51.6 μL, 43 mg, 0.5 mmol) and an internal standard [(Me$_3$Si)$_4$C], and acetone-d$_6$ to bring the total volume to 1 mL. The proton NMR spectrum was acquired. In the glovebox, the catalyst (4.6 mg, 0.01 mmol) was added. Outside the glovebox, the NMR tube was then placed in an oil bath at 70° C. Observation of the mixture by NMR spectroscopy after 1, 2, and 5 h revealed that pentanal had been formed in over 95% yield after 5 h. $^1$H NMR of the product in the mixture (CD$_3$COCD$_3$, 500 MHz) δ 0.90 (t, 3H, J=7 Hz), 1.33-1.36 (m, 2H), 1.54-1.60 (m, 2H), 2.04-2.06 (m, 2H), 2.42 (dt, J=1.8, 7 Hz), 9.72 (t, 1H, J=1.8 Hz).

Examples 5 and 6

The following example describes an exemplary method of this invention using an exemplary ruthenium-comprising catalyst composition of this invention.

In a further example the exemplary catalyst of Formula V is shown isomerizing 1-pentene to a mixture of isomers within 1 hour at room temperature using only 2 mol % of catalyst (Scheme VII). In another embodiment, a catalyst of this invention is illustrated isomerizing 4-penten-1-ol to the aldehyde pentanal (Scheme VIII).

In the pentenol case, isomerization proceeds through several stages. E- and Z-1 penten-1-ol is the most stable of the alkene isomers and then a final equilibration between the keto and enol leading to a pure aldehyde (greater than 95% yield). In these exemplary reactions of the invention, the acetone used in Scheme VI is substituted with THF (Scheme VII) and with methylene chloride (Scheme VIII). In a variation of this exemplary reaction of the invention, it has been determined that using 5 mol % of the catalyst at room temperature allows isomerization to complete in 1 to 2 days.

Example 3

The following example describes an exemplary method for making an exemplary ruthenium-comprising catalyst composition of this invention.

In this embodiment, the exemplary catalyst of Formula VI can be formed

Formula VI

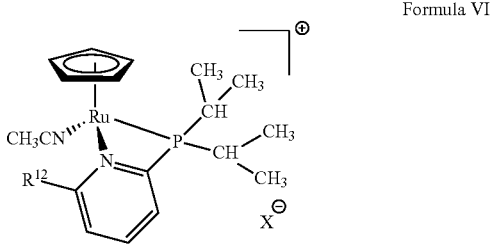

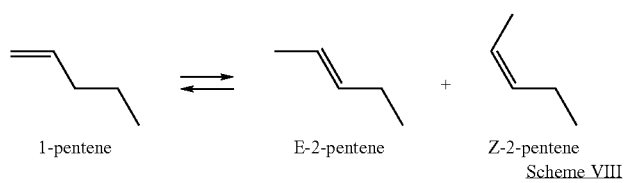

Scheme VII

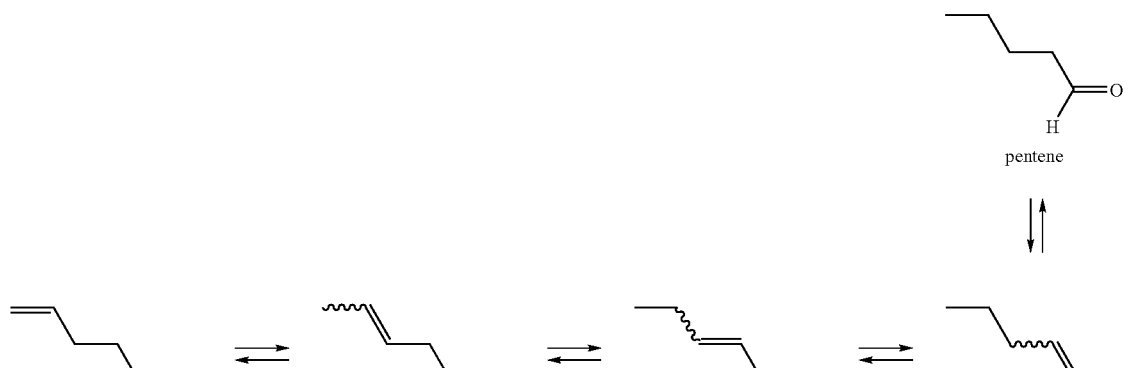

Scheme VIII

Example 7

The following example describes an exemplary method of this invention using an exemplary ruthenium-comprising catalyst composition of this invention.

Another embodiment of the invention using an invention's bifunctional catalyst, octadec-9-en-1,18-diol can be isomerized to the unsymmetrical compound 18-hydroxyoctadecanal, a process which must involve moving the double bond past 8 carbon atoms. If one were to try performing this isomerization process using the prior art method of hydrogenating and then selectively oxidizing one alcohol only, it would be difficult or impossible to do so in over 50% yield. However, using the catalysts of the current invention, yield is over 90% without wasting any reactant. Thus, these catalysts of the invention are useful for moving a double bond across numerous carbon atoms.

Scheme IX

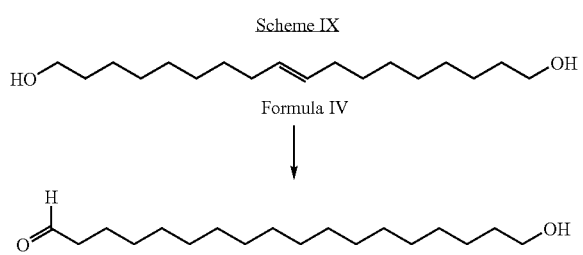

Formula IV

Example 8

The following example describes an exemplary method of this invention using an exemplary ruthenium-comprising catalyst composition of this invention.

Using an ether of 4-penten-1-ol ($R^{14}$=tBuPh$_2$Si), with the catalysts of the invention, the reaction is done within hours using 2 mol % catalyst at 70° C. and a nearly pure E isomer is formed. The exemplary Formula IV catalyst is used as described above.

Scheme X

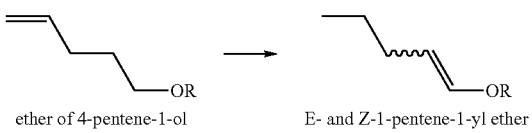

Example 9

The following example describes an exemplary method of this invention using an exemplary ruthenium-comprising catalyst composition of this invention.

Another embodiment illustrates the versatility of the bifunctional catalysts of this invention, alkenes are deuterated. In this example, 1-pentene is isomerized using 5 mol % catalyst (Formula IV) in the presence of 10 equiv. D$_2$O at room temperature. $^1$H NMR spectra of the mixture over time showed the complete isomerization of pentene within 1 hour followed by a slower (36 hour) incorporation of deuterium in to all positions of the alkene.

Scheme XI

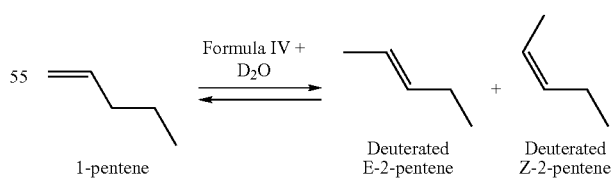

Example 10

Isomerization of Linoleic Acid at 70° C.

The following example describes an exemplary method of this invention using an exemplary ruthenium-comprising catalyst composition of this invention.

Linoleic acid (101.3 mg, 0.37 mmol) and 5 mol % catalyst 1 (11.5 mg, 0.019 mmol) were dissolved in oxygen-free acetone-$d_6$ (1.0 mL) in a resealable NMR tube. For linoleic acid in the mixture: $^1$H NMR (500 MHz, acetone-$d_6$) δ 5.29-5.41 (m, 4H), 2.80 (t, J=6.5, 2H), 2.28 (t, J=7.5, 2H), 2.02-2.13 (m, 4H), 1.59 (quintet, J≈7.5, 2H), 1.26-1.41 (m, 14H), 0.89 ppm (~t, J≈7, 3H). For the products in the mixture: (500 MHz, acetone-$d_6$) δ 6.30-6.39 (m, 1H), 5.94 (t, J=10.5, 1H), 5.65 (td, J=7.5, 15, 1H), 5.24-5.32 (m, 1H), 2.28 (t, J=7.5, 2H), 2.13-2.20 (m, 2H), 2.10 (~q, J≈7.5, 2H), 1.54-1.63 (m, 2H), 1.24-1.44 (m, 14H), 0.85-0.92 ppm (m, 3H).

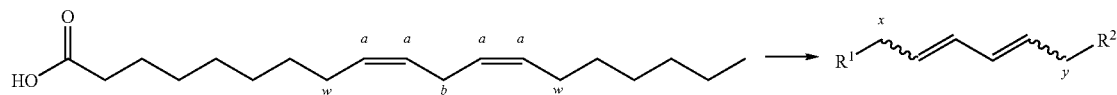

Preservation of the allylic protons can be seen as the integrals are maintained over the duration of the reaction. This further concludes the product has become conjugated.

TABLE 5

Integrations in arbitrary units of key $^1$H NMR signals for the starting compound, linoleic acid, and conjugated product. The value of the integral for the singlet due to the internal standard, $(Me_3Si)_4C$, was set equal to 10.00 integral units in each case. Data was acquired using a Varian 500 MHz spectrophotometer, with sixteen 15° pulses and 20 second delays between pulses. The remaining $^1$H resonances for starting material and product overlapped and so were not used.

|  | Time at 70° C. | | |
| --- | --- | --- | --- |
|  | 0 h | 90 min | 2.5 h |
| Protons a 5.29-5.41 ppm | 67.38 | NA | NA |
| Protons b 2.80 ppm | 33.54 | 0.86 | 0 |
| Units per proton | 16.82 | 0.43 | 0 |
| % starting material | 100 | 2.6 | 0 |
| Protons x$^d$ 2.13-2.20 ppm | 0 | 30.73 | 31.76 |
| Protons y$^d$ 2.10 ppm | 0 | 31.06 | 30.52 |
| Units per Proton | 0 | 15.45 | 15.57 |
| % conjugated product | 0 | 91.9 | 92.6 |

$^a$Calculated by dividing units per proton of starting material at time indicated by units per proton value at hour 0.
$^b$Calculated by taking the average of integrations of the specified resonances.
$^c$Calculated by dividing units per proton of product at time indicated by the units per proton value of starting material at hour 0.
$^d$Integrations may be skewed due to overlap with neighboring peaks or solvent signals. NA is not available due to overlap.

Example 11

Isomerization of Methyl Linoleate at 70° C.

The following example describes an exemplary method of this invention using an exemplary ruthenium-comprising catalyst composition of this invention.

Same as entry 1, but methyl linoleate (102.9 mg, 0.35 mmol) and 1 mol % catalyst 1 (2.3 mg, 0.0038 mmol) was used. For methyl linoleate in the mixture: $^1$H NMR (500 MHz, acetone-$d_6$) δ 5.28-5.41 (m, 4H), 3.60 (s, 3H), 2.79 (t, J=6.5, 2H), 2.28 (t, J=7.5, 2H), 2.02-2.12 (m, 4H), 1.59 (quintet, J≈7, 2H), 1.23-1.45 (m, 14H), 0.89 ppm (~t, J≈7, 3H). For the products in the mixture: (500 MHz, acetone-$d_6$) δ 6.29-6.41 (m, 1H), 5.93 (t, J=11, 1H), 5.65 (td, J=7.5, 15, 1H), 5.23-5.32 (td, J=7.5, 11, 1H), 3.60 (s, 3H), 2.28 (t, J=7.5, 2H), 2.06-2.20 (m, 4H), 1.58 (~quintet, J≈7.5, 2H), 1.23-1.45 (m, 14H), 0.84-0.92 ppm (m, 3H).

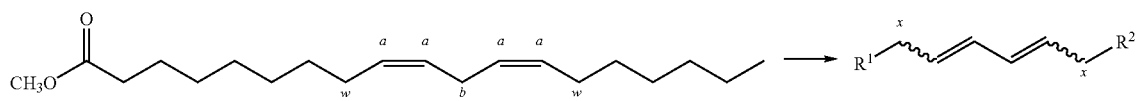

Preservation of the allylic protons can be seen as the integrals are maintained over the duration of the reaction.

TABLE 6

Integrations in arbitrary units of key $^1$H NMR signals for the starting compound, methyl linoleate, and conjugated product. The value of the integral for the singlet due to the internal standard, $(Me_3Si)_4C$, was set equal to 10.00 integral units in each case. Data was acquired using a Varian 500 MHz spectrophotometer, with sixteen 15° pulses and 20 second delays between pulses. The remaining $^1$H resonances for starting material and product overlapped and so were not used.

|  | Time at 70° C. | | | |
|---|---|---|---|---|
|  | 0 h | 1 h | 2 h | 4 h |
| Protons a 5.28-5.41 ppm | 115.48 | NA | NA | NA |
| Protons b 2.80 ppm | 58.03 | 12.94 | 5.91 | 0 |
| Units per proton | 28.92 | 6.47 | 2.96 | 0 |

TABLE 6-continued

Integrations in arbitrary units of key $^1$H NMR signals for the starting compound, methyl linoleate, and conjugated product. The value of the integral for the singlet due to the internal standard, $(Me_3Si)_4C$, was set equal to 10.00 integral units in each case. Data was acquired using a Varian 500 MHz spectrophotometer, with sixteen 15° pulses and 20 second delays between pulses. The remaining $^1$H resonances for starting material and product overlapped and so were not used.

|  | Time at 70° C. | | | |
|---|---|---|---|---|
|  | 0 h | 1 h | 2 h | 4 h |
| % starting material | 100 | 22.3 | 10.2 | 0 |
| Alkene Proton 6.30-6.39 | 0 | 22.24 | 24.66 | 23.61 |
| Alkene Proton 5.94 | 0 | 22.26 | 24.69 | 23.46 |
| Units per Proton | 0 | 22.25 | 24.68 | 23.54 |
| % product | 0 | 76.7 | 85.0 | 81.1 |
| All allylic protons $w + x^d$ | 0 | 117.5 | 119.69 | 110.66 |
| Units per Proton | 0 | 29.38 | 29.94 | 27.66 |

$^a$Calculated by dividing units per proton of starting material at time indicated by units per proton value at hour 0.
$^b$Calculated by taking the average of integrations of the specified resonances.
$^c$Calculated by dividing units per proton of product at time indicated by the units per proton value of starting material at hour 0.
$^d$Integration includes peak value and acetone solvent value. Reliable unit per proton value was obtained and subtracted from the initial total integral, of proton signal and acetone solvent signal, at time 0 to obtain the reliable acetone value. At each time, this value of acetone was subtracted from the total integral to obtain the value for protons w + x.
NA is not available due to overlap.

Example 12

Isomerization of Methyl Linolenate at 70° C.

The following example describes an exemplary method of this invention using an exemplary ruthenium-comprising catalyst composition of this invention.

Same as entry 1, but methyl linolenate (52.9 mg, 0.18 mmol) and 2.4 mol % catalyst 1 (2.7 mg, 0.0044 mmol) were used. For methyl linoleate in the mixture: $^1$H NMR (500 MHz, acetone-$d_6$) δ 5.26-5.43 (m, 6H, H$^a$), 3.60 (s, 3H), 2.78-2.88 (m, 4H, H$^b$), 2.28 (t, J=7.5, 2H, H$^c$), 2.05-2.13 (m, 4H, H$^w$), 1.55 (~quintet, J≈7.5, 2H), 1.27-1.42 (m, 12H), 0.96 ppm (t, J=7.5, 3H). For the products in the mixture: (500 MHz, acetone-$d_6$) δ 3.61 (s, 3H), 2.29 (t, J=7.5, 2H), 2.07-2.22 (m, 4H, H$^b$), 1.58 (~quintet, J≈7, 2H), 1.25-1.45 (m, 12H).

During the course of the reaction, the signals for the methylene protons between the skipped double bonds (H$^b$) disappear completely, consistent with conjugation of the double bonds. In addition, the total integral for the methylene protons adjacent to a single double bond (chemical shift between 2.05 and 2.22 ppm) stays nearly constant, as required for the products shown. If only one double bond moved into conjugation, leaving the third double bond isolated, one would expect integrals corresponding to 8 allylic protons.

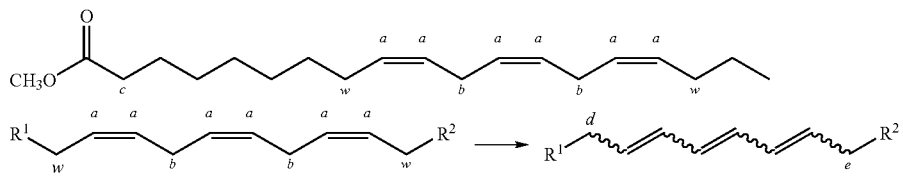

TABLE 7

Integrations in arbitrary units of key $^1$H NMR signals for the starting compound, methyl linolenate, and conjugated product. Other comments same as for Table 5.

|  | Time at 70° C. | | | |
|---|---|---|---|---|
|  | 0 h | 1 h | 2 h | 22 h |
| Protons a 5.26-5.43 ppm | 53.61 | NA | NA | NA |
| CH$_3$OC(O)—R 3.60 ppm | 26.86 | NA | NA | NA |
| Protons b 2.78-2.88 ppm | 36.05 | 2.59 + 4.85 | 1.33 + 2.98 | 0 |
| Protons c 2.28 ppm | 18.27 | NA | NA | NA |
| Units per proton | 8.99 | 1.86 | 1.08 | 0 |
| % starting material | 100 | 20.7 | 12.0 | 0 |
| All allylic protons w + d + e$^d$ 2.07-2.22 ppm | 0 | 50.1 | 51.3 | 45.1 |
| Units per Proton | 0 | 12.5 | 12.8 | 11.3 |
| % Conjugated Product | 0 | 79.3 | 88.0 | 100 |

$^a$Calculated by dividing units per proton of starting material at time indicated by units per proton value at hour 0.
$^b$Calculated by taking the average of integrations of the specified resonances.
$^c$Calculated by dividing units per proton of product at time indicated by the units per proton value of starting material at hour 0.
$^d$Integration includes peak value and acetone solvent value. Reliable unit per proton value was obtained and subtracted from the initial total integral, of proton signal and acetone solvent signal, at time 0 to obtain the reliable acetone value. At each time, this value of acetone was subtracted from the total integral to obtain the value for Protons d + e.
NA is not available due to overlap.

While the invention has been described in detail with reference to certain preferred aspects thereof, it will be understood that modifications and variations are within the spirit and scope of that which is described and claimed.

What is claimed is:

1. An immobilized composition comprising a structure selected from a group consisting of a formula as set forth in Formula 1, 2, and 2b structures:

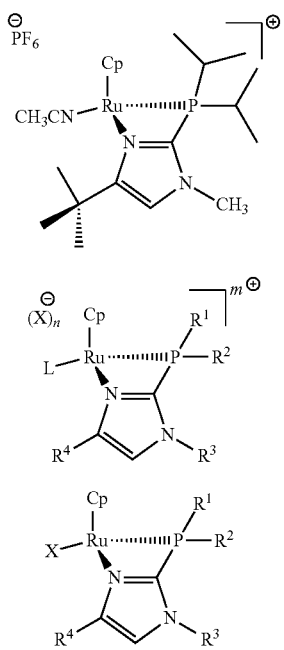

wherein independently:

$R^1$ is $CH_3CN$, or a halide, a hydride, a carboxylate, a sulfonate, or any neutral or anionic ligand;

$R^2$ is $CH_3CN$, or a halide, a hydride, a carboxylate, a sulfonate, or any neutral or anionic ligand, or $R^1$, $R^2$, $R^3$, and $R^4$ can each separately and independently be a hydrogen, $CH(CH_3)_2$, $C(CH_3)_2$, or any alkyl or aryl group, including heteroaryl, or any other substituent, and L is $CH_3CN$, halide, hydride, carboxylate, sulfonate, or any neutral or anionic ligand, X is an anion, and optionally a halide, a hydride, a carboxylate or a sulfonate, m is a cation having an appropriate balance of charge for anion X when the overall charge of the complex is zero, p is $C_5H_5$ or a $C_5H_5$ substituted with an alkyl or an aryl group or groups or a heteroaryl, or Cp is an indenyl or benzene, or an indenyl or benzene substituted with an alkyl or an aryl group or groups, or an heteroaryl, or a Tp (tris-pyrazolylborate) or a Tp substituted with an alkyl or an aryl group or groups, or a heteroaryl, and the composition is immobilized.

2. An alkene isomerization catalyst comprising the immobilized composition of claim 1.

3. A method for alkene isomerization for converting a polyunsaturated organic molecule comprising two or more skipped (or non-conjugated) double bonds, to their conjugated isomers having conjugated double bonds, comprising
(i) (a) providing the immobilized composition of claim 1, and
(b) contacting the immobilized composition or alkene isomerization catalyst with the polyunsaturated organic molecule under conditions wherein the skipped (or non-conjugated) double bonds are isomerized to a conjugated double bond isomer form.

4. A method for conjugating at least two double bonds in a non-conjugated double bond-comprising hydrocarbon substance or polymer to generate a conjugated isomer thereof having conjugated double bonds, comprising
(i) (a) providing the immobilized composition of claim 1, and
(b) contacting the non-conjugated double bond-comprising composition with the immobilized composition or alkene isomerization catalyst of (a) under conditions wherein two or several of the skipped (or nonconjugated) double bonds are isomerized to a conjugated double bond isomer form.

5. A method for making a conjugated linoleic acid or methyl linoleate comprising use of the immobilized composition of claim 1, as a catalyst for conjugating double bonds.

6. A product of manufacture comprising: the immobilized composition of claim 1.

7. A kit comprising: the immobilized composition of claim 1.

8. A liquid formulation comprising: the immobilized composition of claim 1.

9. A resin or a solid or semisolid or a gel support having immobilized thereon a composition of claim 1.

10. A composition comprising
(a) a polyunsaturated organic molecule; and (b) the immobilize composition of claim 1.

11. The immobilized composition of claim 1, wherein the ruthenium is replaced (substituted) by a metal selected from the group consisting of a transition metal, a 1+, 2+, or 3+ oxidation state transition metal, a group 6, 7, 8, or 9 transition metal, chromium, molybdenum, tungsten, manganese, rhenium, iron, ruthenium, osmium, cobalt, rhodium, iridium, nickel, palladium, platinum, copper, silver and gold.

12. The method of claim 3, wherein the non-conjugated double bonds are separated by a methylene group, an ethylene group, a propylene or a longer group.

13. The method of claim 3, wherein the polyunsaturated organic molecule comprises or is: a triglyceride, fat, oil or derivative therefrom, or a fatty acid, or a polyunsaturated fatty acid, triglyceride, fat, oil or a derivative thereof.

14. The method of claim 13, wherein the polyunsaturated organic molecule is or is derived from a linoleic acid, a linseed, a fish, a soybean, a tall, a tung, a corn, a sunflower, a safflower, a castor and/or oiticica oil and/or a fat.

15. The method of claim 13, wherein the polyunsaturated organic molecule or triglyceride, fat, oil or derivative therefrom comprises, or is derived from linoleic acid or methyl linoleate.

16. The composition of claim 10, wherein the polyunsaturated organic molecule is or comprises a triglyceride, a fat, an oil, a fatty acid, a linoleic acid, a linseed oil, fish oil and/or fat, soybean oil and/or fat, tung oil and/or fat, corn oil and/or fat, sunflower oil and/or fat, safflower oil and/or fat, castor oil and/or fat and/or an oiticica oil and/or a fat.

17. The resin or a solid or semisolid support of claim 9, wherein the resin comprises a cellulose resin, a ethylsulfoxycellulose, a carboxymethyl cellulose or a hydroxyethyl cellulose resin, a fluorine-containing resin, a polymeric resin, urethane resin, an epoxy resin, a polyester resin, a phenol resin, a melamine resin, and/or a silicone resin.

18. The resin or a solid or semisolid support of claim 9, comprising an inorganic material, an inorganic solid, a silica, an alumina or a clay; or an organic material, or an aluminum stearate.

19. The resin or a solid or semisolid support of claim 9, wherein the solid or semisolid support is a nanoparticle.

20. The method of claim 4, wherein:
(i) the non-conjugated double bonds are separated by a methylene group, an ethylene group, a propylene or a longer group;
(ii) all the non-conjugated double bonds are conjugated in the isomer;
(iii) the double bond-comprising hydrocarbon substance or polymer comprises or is a polyunsaturated organic molecule, a triglyceride, fat, oil or derivative therefrom, or a fatty acid, or a polyunsaturated fatty acid, triglyceride, fat, oil or a derivative thereof;
(iv) the reaction conditions comprise anywhere between about 0.01 mol % catalyst and 10 mol % catalyst, or between about 0.5 mol % catalyst and 1.0 mol % catalyst, or between about 1.0 mol % catalyst and 5.0 mol % catalyst, or 1, 2, 3, 4, 5, 6, 7, 8, 9 or 10 or more mol % catalyst, or about 2.4 mol catalyst;
(v) the reaction conditions comprise a temperature in a range from about 60° C. to about 80 or a temperature at about 65° C., 66° C., 67° C., 68° C., 69° C., 70° C., 71° C., 72° C., 73° C., 74° C. or 75° C. or more; or
(vi) the reaction conditions comprise an oxygen-free environment, or, the oxygen-free environment comprises use of an oxygen-free acetone, and the catalyst is dissolved in the acetone.

* * * * *